(12) United States Patent
Amorde et al.

(10) Patent No.: US 11,698,717 B2
(45) Date of Patent: Jul. 11, 2023

(54) SESSION CONTROL FOR A VAPORIZER DEVICE

(71) Applicant: JUUL Labs, Inc., San Francisco, CA (US)

(72) Inventors: Eric Amorde, Oakland, CA (US); Nicolas Dor, San Francisco, CA (US); Randall Leberknight, San Jose, CA (US); Mario Trujillo, San Francisco, CA (US); Raffi Aghapekian, Alameda, CA (US); James Monsees, San Francisco, CA (US); Nicholas J. Hatton, Oakland, CA (US); Brian M. Warren, San Francisco, CA (US); Casey S. Yost, Daly City, CA (US); Nicholas Achtien, San Francisco, CA (US); Travis I. Wyatt, Oakland, CA (US); Roxolana Wacyk, San Francisco, CA (US)

(73) Assignee: JUUL Labs, Inc., Washington, DC (US)

( * ) Notice: Subject to any disclaimer, the term of this patent is extended or adjusted under 35 U.S.C. 154(b) by 785 days.

(21) Appl. No.: 16/442,170

(22) Filed: Jun. 14, 2019

(65) Prior Publication Data

US 2019/0380388 A1 Dec. 19, 2019

Related U.S. Application Data

(60) Provisional application No. 62/685,873, filed on Jun. 15, 2018.

(51) Int. Cl.
*A61M 15/06* (2006.01)
*A24F 40/53* (2020.01)
(Continued)

(52) U.S. Cl.
CPC ............ *G06F 3/0484* (2013.01); *A24F 40/53* (2020.01); *A24F 40/65* (2020.01); *A61M 11/041* (2013.01);
(Continued)

(58) Field of Classification Search
CPC .... A61M 11/041; A61M 16/18; A61M 15/06; A61M 2205/3653; A61M 2205/505;
(Continued)

(56) References Cited

U.S. PATENT DOCUMENTS 8,869,793 B1 * 10/2014 Spandorfer ....... A61M 15/0081
128/203.14
8,991,402 B2 3/2015 Bowen et al.
(Continued)

FOREIGN PATENT DOCUMENTS

EP 1471955 B1 3/2015
EP 3160565 B1 8/2021
(Continued)

*Primary Examiner* — Timothy A Stanis
(74) *Attorney, Agent, or Firm* — Mintz, Levin, Cohn, Ferris, Glovsky and Popeo, P.C.

(57) ABSTRACT

Features relating to vaporizer devices configured to allow for user control of a vaporizer session are provided. Session size selection and temperature selection options allow for a user to select a desired session size and a desired temperature for the vaporizer session. A session control user interface is provided on a user device to allow for user selections and to provide for user viewing of a status of the vaporizer session.

56 Claims, 19 Drawing Sheets

(51) Int. Cl.
*G06F 3/0484* (2022.01)
*A61M 11/04* (2006.01)
*A61M 16/18* (2006.01)
*A24F 40/65* (2020.01)

(52) U.S. Cl.
CPC ............ *A61M 16/18* (2013.01); *A61M 15/06* (2013.01); *A61M 2205/3653* (2013.01); *A61M 2205/505* (2013.01); *A61M 2205/60* (2013.01); *A61M 2205/8212* (2013.01)

(58) Field of Classification Search
CPC ....... A61M 2205/60; A61M 2205/8212; A24F 40/40; A24F 40/46; A24F 40/50; A24F 40/57
See application file for complete search history.

(56) References Cited

U.S. PATENT DOCUMENTS

| | | | |
|---|---|---|---|
| 9,427,022 B2 | 8/2016 | Levin et al. | |
| 9,687,027 B2 | 6/2017 | Poston et al. | |
| 9,763,478 B2 | 9/2017 | Cameron et al. | |
| 9,770,055 B2 | 9/2017 | Cameron et al. | |
| 9,802,011 B2 | 10/2017 | Davidson et al. | |
| 9,888,723 B2 | 2/2018 | Cameron et al. | |
| 10,058,128 B2 | 8/2018 | Cameron et al. | |
| 10,065,005 B2 | 9/2018 | Wilder et al. | |
| 10,085,486 B2 | 10/2018 | Cameron | |
| 10,292,427 B2 | 5/2019 | Cameron et al. | |
| 10,517,331 B2 | 12/2019 | Atkins et al. | |
| 2011/0202495 A1* | 8/2011 | Gawlick | G16H 50/20 600/301 |
| 2012/0048266 A1* | 3/2012 | Alelov | A61M 11/042 128/203.14 |
| 2013/0276799 A1 | 10/2013 | Davidson et al. | |
| 2013/0333702 A1* | 12/2013 | Baloa Welzien | A61M 16/0069 128/204.21 |
| 2015/0136158 A1 | 5/2015 | Stevens et al. | |
| 2016/0166564 A1 | 6/2016 | Myers et al. | |
| 2016/0324217 A1 | 11/2016 | Cameron | |
| 2016/0325055 A1 | 11/2016 | Cameron | |
| 2016/0331022 A1 | 11/2016 | Cameron | |
| 2016/0331023 A1 | 11/2016 | Cameron | |
| 2016/0331024 A1 | 11/2016 | Cameron | |
| 2016/0331025 A1 | 11/2016 | Cameron | |
| 2016/0331026 A1 | 11/2016 | Cameron | |
| 2016/0331027 A1 | 11/2016 | Cameron | |
| 2016/0331034 A1 | 11/2016 | Cameron | |
| 2016/0331036 A1* | 11/2016 | Cameron | H04Q 9/00 |
| 2016/0331859 A1 | 11/2016 | Cameron | |
| 2016/0334119 A1 | 11/2016 | Cameron | |
| 2016/0334847 A1 | 11/2016 | Cameron | |
| 2016/0337141 A1 | 11/2016 | Cameron | |
| 2016/0337362 A1 | 11/2016 | Cameron | |
| 2016/0337444 A1 | 11/2016 | Cameron | |
| 2016/0356751 A1 | 12/2016 | Blackley | |
| 2016/0363570 A1 | 12/2016 | Blackley | |
| 2016/0363917 A1 | 12/2016 | Blackley | |
| 2016/0367925 A1 | 12/2016 | Blackley | |
| 2016/0370335 A1 | 12/2016 | Blackley | |
| 2017/0018000 A1 | 1/2017 | Cameron | |
| 2017/0020188 A1 | 1/2017 | Cameron | |
| 2017/0020195 A1 | 1/2017 | Cameron | |
| 2017/0020196 A1 | 1/2017 | Cameron | |
| 2017/0020197 A1 | 1/2017 | Cameron | |
| 2017/0027229 A1 | 2/2017 | Cameron | |
| 2017/0042230 A1* | 2/2017 | Cameron | A24F 40/60 |
| 2017/0042231 A1 | 2/2017 | Cameron | |
| 2017/0046357 A1 | 2/2017 | Cameron | |
| 2017/0046738 A1 | 2/2017 | Cameron | |
| 2017/0055588 A1 | 3/2017 | Cameron | |
| 2017/0086496 A1 | 3/2017 | Cameron | |
| 2017/0086497 A1 | 3/2017 | Cameron | |
| 2017/0086503 A1 | 3/2017 | Cameron | |
| 2017/0086504 A1 | 3/2017 | Cameron | |
| 2017/0091853 A1 | 3/2017 | Cameron | |
| 2017/0092106 A1 | 3/2017 | Cameron | |
| 2017/0093960 A1 | 3/2017 | Cameron | |
| 2017/0093981 A1 | 3/2017 | Cameron | |
| 2017/0119058 A1 | 5/2017 | Cameron | |
| 2017/0127727 A1 | 5/2017 | Davidson et al. | |
| 2017/0127945 A1* | 5/2017 | Reed | A61M 11/00 |
| 2017/0135407 A1 | 5/2017 | Cameron | |
| 2017/0135408 A1 | 5/2017 | Cameron | |
| 2017/0135409 A1 | 5/2017 | Cameron | |
| 2017/0135411 A1 | 5/2017 | Cameron | |
| 2017/0135412 A1 | 5/2017 | Cameron | |
| 2017/0136193 A1 | 5/2017 | Cameron | |
| 2017/0136194 A1 | 5/2017 | Cameron | |
| 2017/0136196 A1 | 5/2017 | Davidson et al. | |
| 2017/0136301 A1 | 5/2017 | Cameron | |
| 2017/0181467 A1 | 6/2017 | Cameron | |
| 2017/0181474 A1 | 6/2017 | Cameron | |
| 2017/0181475 A1 | 6/2017 | Cameron | |
| 2017/0185364 A1 | 6/2017 | Cameron | |
| 2017/0231283 A1 | 8/2017 | Gadas | |
| 2017/0303590 A1 | 10/2017 | Cameron et al. | |
| 2017/0303593 A1 | 10/2017 | Cameron et al. | |
| 2017/0303594 A1 | 10/2017 | Cameron et al. | |
| 2017/0309091 A1 | 10/2017 | Cameron et al. | |
| 2017/0332702 A1 | 11/2017 | Cameron et al. | |
| 2018/0043114 A1 | 2/2018 | Bowen et al. | |
| 2018/0077967 A1 | 3/2018 | Hatton et al. | |
| 2018/0153219 A1* | 6/2018 | Verleur | A24F 40/40 |
| 2018/0177231 A1 | 6/2018 | Woodbine et al. | |
| 2019/0014824 A1* | 1/2019 | Yazbeck | A61M 15/06 |
| 2019/0029319 A1* | 1/2019 | Moorman | A24F 9/02 |
| 2019/0158938 A1 | 5/2019 | Bowen et al. | |
| 2019/0200677 A1 | 7/2019 | Chong et al. | |
| 2019/0289915 A1* | 9/2019 | Heidl | G06F 3/016 |
| 2020/0352249 A1 | 11/2020 | Achtien et al. | |

FOREIGN PATENT DOCUMENTS

| | | |
|---|---|---|
| EP | 3621466 B1 | 12/2021 |
| WO | WO-2019104227 A1 | 5/2019 |
| WO | WO-2019126805 A1 | 6/2019 |
| WO | WO-2019173923 A1 | 9/2019 |

* cited by examiner

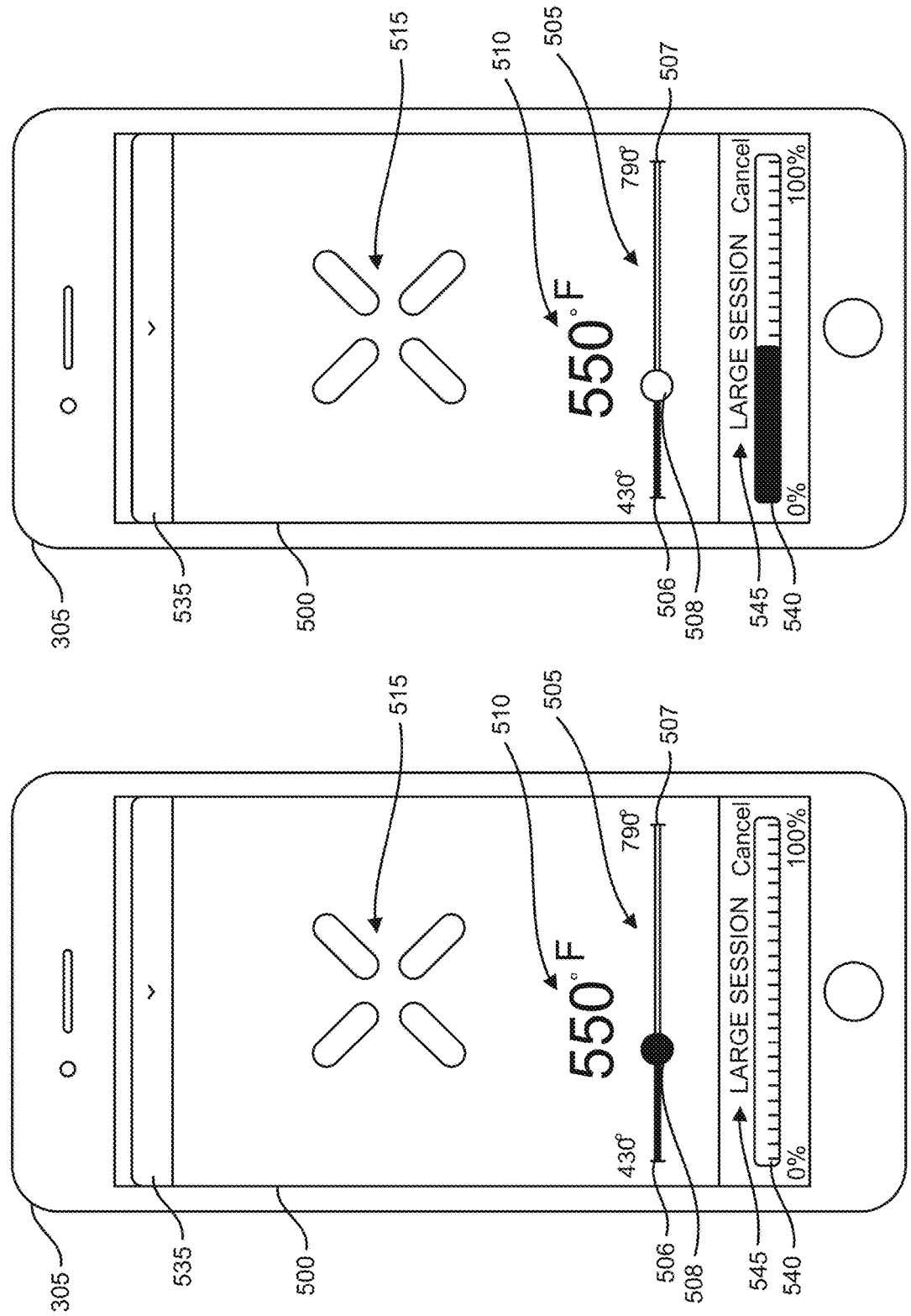

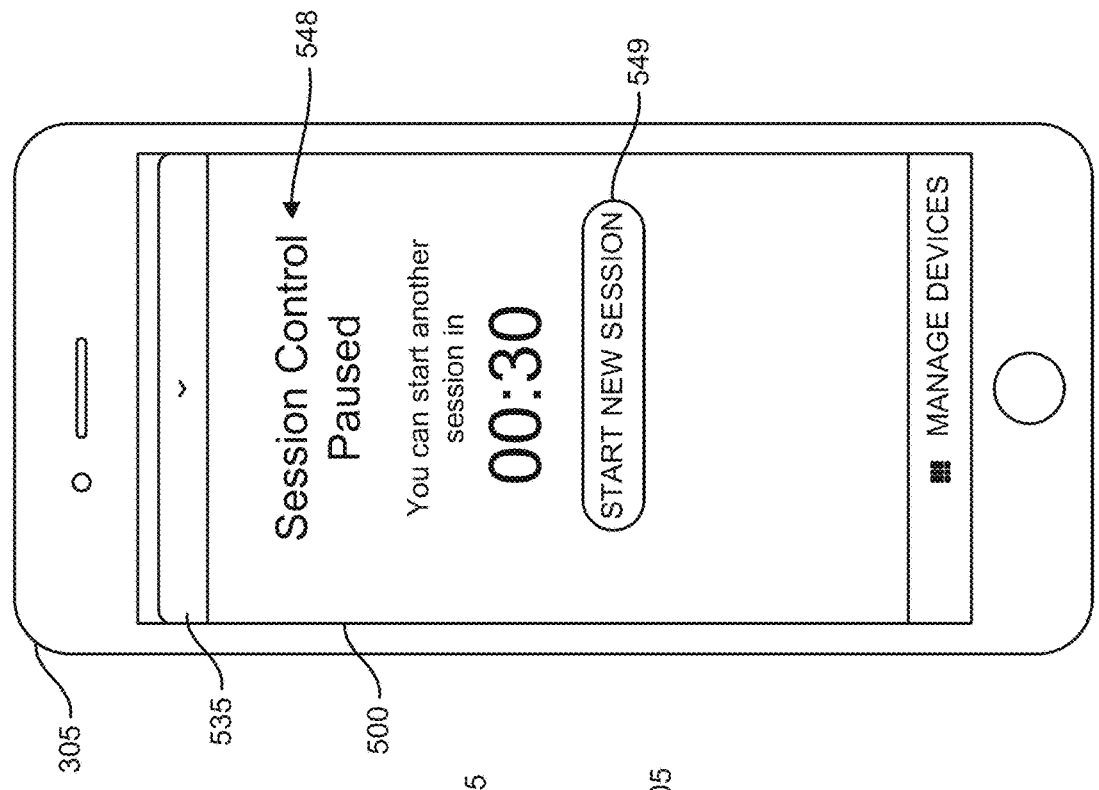
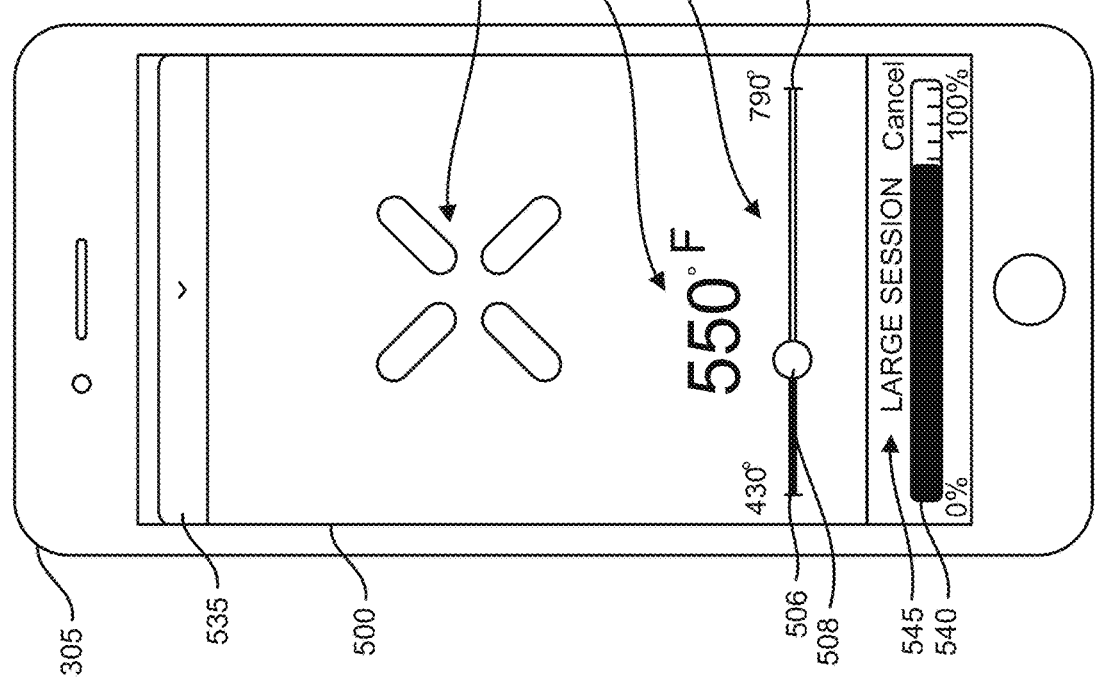

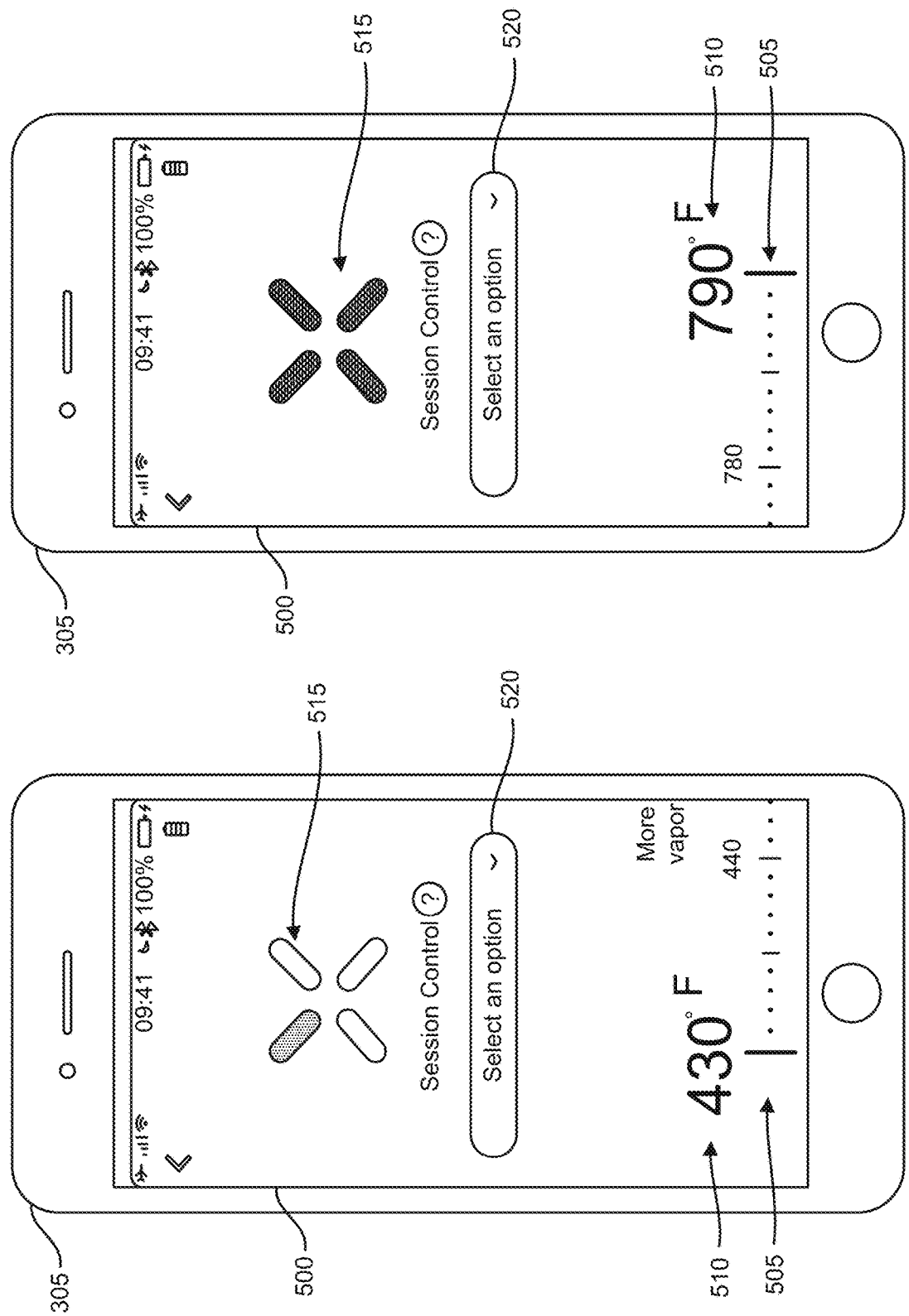

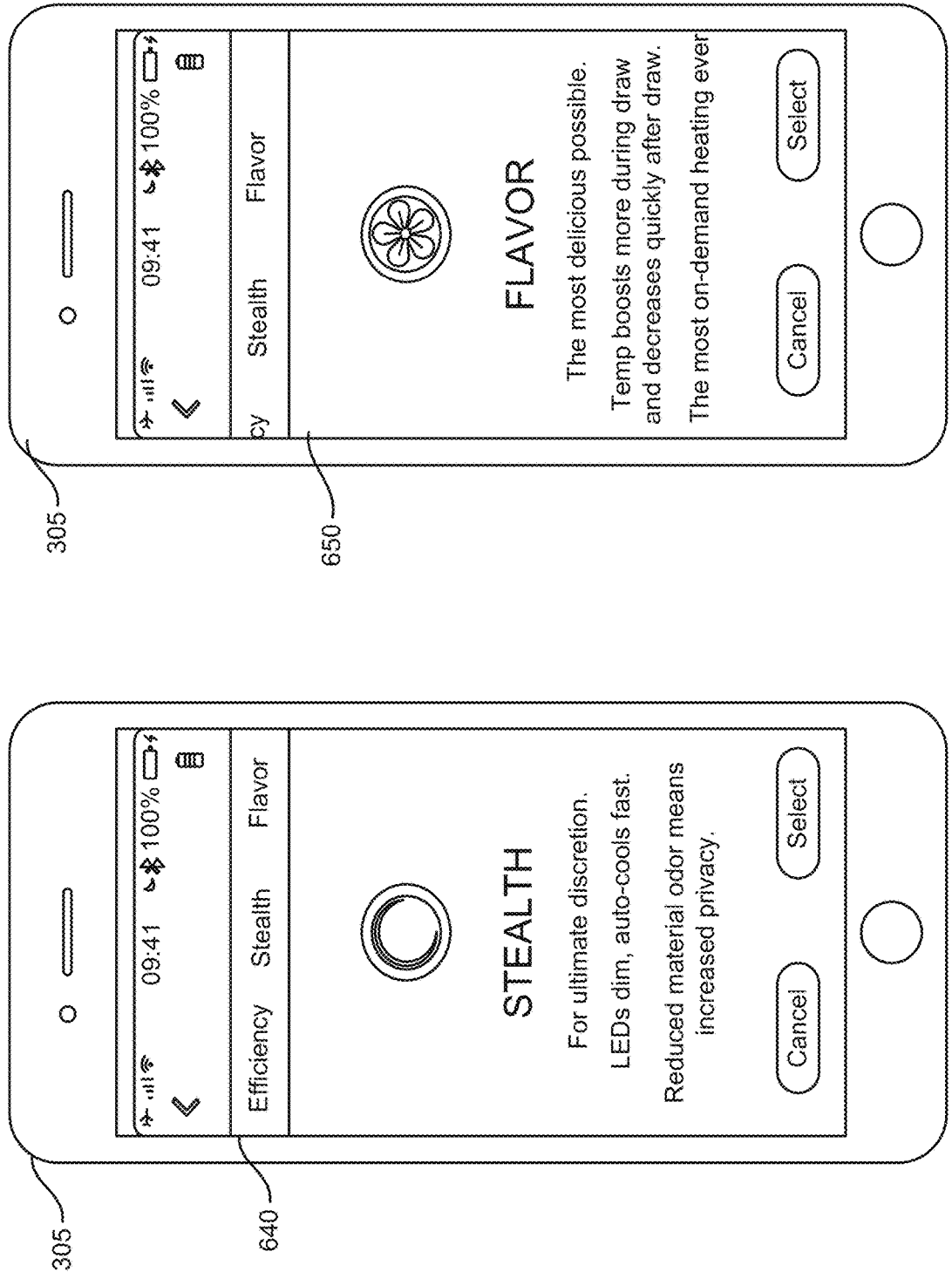

SESSION CONTROL FOR A VAPORIZER DEVICE

CROSS-REFERENCE TO RELATED APPLICATIONS

This application claims priority to U.S. Provisional Patent Application No. 62/685,873, filed on Jun. 15, 2018, incorporated herein by reference in its entirety.

TECHNICAL FIELD

The current subject matter described herein relates generally to vaporizer devices, such as portable, personal vaporizer devices for generating and delivering an inhalable aerosol from one or more vaporizable materials, and more particularly relates to vaporizer devices configured to allow for user control of an amount of vapor consumed.

BACKGROUND

Vaporizing devices, including electronic vaporizers or e-vaporizer devices, allow the delivery of vapor and aerosol containing one or more active ingredients by inhalation of the vapor and aerosol. Electronic vaporizer devices are gaining increasing popularity both for prescriptive medical use, in delivering medicaments, and for consumption of nicotine, tobacco, other liquid-based substances, and other plant-based smokeable materials, such as cannabis, including solid (e.g., loose-leaf or flower) materials, solid/liquid (e.g., suspensions, liquid-coated) materials, wax extracts, and prefilled pods (cartridges, wrapped containers, etc.) of such materials. Electronic vaporizer devices in particular may be portable, self-contained, and convenient for use.

SUMMARY

Aspects of the current subject matter relate to controlling a session and a temperature of one or more vaporizable materials being vaporized and inhaled by a user of a vaporizer device.

According to an aspect of the current subject matter, a method includes providing a user interface including a dropdown menu and a slideable selection bar, the dropdown menu including a plurality of selectable session size options for a vaporizer session of a vaporizer device, and the slideable selection bar including a slideable icon configured to select a temperature for the vaporizer session of the vaporizer device; receiving, from the user interface, a session size selection and a temperature selection; providing, on the user interface, a temperature icon representative of the temperature selection; providing, on the user interface, a status bar indicative of progress through the vaporizer session, where the vaporizer session is based on the session size selection and the temperature selection; and updating, on the user interface, the status bar to reflect the progress through the vaporizer session.

According to an inter-related aspect, an apparatus includes at least one data processor and at least one memory storing instructions which, when executed by the at least one data processor, cause operations including providing a user interface on the apparatus, the user interface including a dropdown menu and a slideable selection bar, the dropdown menu including a plurality of selectable session size options for a vaporizer session of a vaporizer device, and the slideable selection bar including a slideable icon configured to select a temperature for the vaporizer session of the vaporizer device, where the apparatus and the vaporizer device are in communication with one another; receiving, from the user interface, a session size selection and a temperature selection; providing, on the user interface, a temperature icon representative of the temperature selection; providing, on the user interface, a status bar indicative of progress through the vaporizer session, where the vaporizer session is based on the session size selection and the temperature selection; and updating, on the user interface, the status bar to reflect the progress through the vaporizer session.

According to an inter-related aspect, a non-transitory computer readable medium is provided, the non-transitory computer readable medium storing instructions, which when executed by at least one data processor, result in operations including providing a user interface including a dropdown menu and a slideable selection bar, the dropdown menu including a plurality of selectable session size options for a vaporizer session of a vaporizer device, and the slideable selection bar including a slideable icon configured to select a temperature for the vaporizer session of the vaporizer device; receiving, from the user interface, a session size selection and a temperature selection; providing, on the user interface, a temperature icon representative of the temperature selection; providing, on the user interface, a status bar indicative of progress through the vaporizer session, where the vaporizer session is based on the session size selection and the temperature selection; and updating, on the user interface, the status bar to reflect the progress through the vaporizer session.

In some variations, one or more of the features disclosed herein including the following features can optionally be included in any feasible combination. Each of the plurality of selectable session size options may correspond to a predetermined amount of energy to apply to a heating element of the vaporizer device. The slideable icon may be configured to be moved along the slideable selection bar between a predefined low end temperature and a predefined high end temperature. In response to a determination that the vaporizer session is in progress, the session size selection and the temperature selection may be locked such that the session size selection and the temperature selection are not adjustable via the user interface while the vaporizer session is in progress. A characteristic of the slideable icon may be changed on the user interface and in response to the determination that the vaporizer session is in progress. Providing the temperature icon representative of the temperature selection may include one or more of providing a first temperature icon including a numerical representation of the temperature selection and providing a second temperature icon including a symbol shaded in correlation with the temperature selection. The status bar may include a horizontally elongated window, where the horizontally elongated window is filled during the vaporizer session indicative of the progress through the vaporizer session. The progress through the vaporizer session may include a cumulative amount of energy provided to a heating element of the vaporizer device over a total amount of energy to be provided to the heating element, where the total amount of energy to be provided is based on the session size selection. Updating the status bar to reflect the progress through the vaporizer session may include filling the horizontally elongated window to represent a fraction comprising the cumulative amount of energy over the total amount of energy. On the user interface and in response to selection of a collapse selection feature, a collapsed window may be provided, the collapsed window providing a representation of the temperature selection, the session size selection, and the status bar. The collapsed window may be expand, on the user interface and in response to selection of the collapsed window. A lock screen indicative of the vaporizer session being completed may be provided, where the lock screen includes a start new session button, where selection of the start new session initiates a new vaporizer session during a lockout period. The lockout period may be predefined and/or non-adjustable.

According to an aspect of the current subject matter, a method includes receiving, by a vaporizer device in communication with a user device, operational data indicative of a selected session size and a selected temperature for a vaporizer session, where the vaporizer device includes a controller, wireless communication circuitry, heater control circuitry, and a heating element; causing the vaporizer device to operate consistent with the operational data indicative of the selected session size and the selected temperature; and providing, by the vaporizer device and to the user device, status data indicative of a status of the vaporizer session.

According to an inter-related aspect, an apparatus includes at least one data processor and at least one memory storing instructions which, when executed by the at least one data processor, cause operations including receiving, from a user device in communication with the apparatus, operational data indicative of a selected session size and a selected temperature for a vaporizer session, where the apparatus comprises a controller, wireless communication circuitry, heater control circuitry, and a heating element; causing the apparatus to operate consistent with the operational data indicative of the selected session size and the selected temperature; and providing, to the user device, status data indicative of a status of the vaporizer session.

According to an inter-related aspect, a non-transitory computer readable medium is provided, the non-transitory computer readable medium storing instructions, which when executed by at least one data processor, result in operations including receiving, by a vaporizer device in communication with a user device, operational data indicative of a selected session size and a selected temperature for a vaporizer session, where the vaporizer device includes a controller, wireless communication circuitry, heater control circuitry, and a heating element; causing the vaporizer device to operate consistent with the operational data indicative of the selected session size and the selected temperature; and providing, by the vaporizer device and to the user device, status data indicative of a status of the vaporizer session.

In some variations, one or more of the features disclosed herein including the following features can optionally be included in any feasible combination. The operational data indicative of the selected session size may include a total amount of energy to be provided to the heating element during the vaporizer session. Causing the vaporizer device to operate may include providing the total amount of energy to the heating element during the vaporizer session. The status data indicative of the status of the vaporizer session may include a cumulative amount of energy provided to the heating element. A determination may be made that the vaporizer session is completed, the determination based on a comparison of a cumulative amount of energy provided to the heating element and the total amount of energy to be provided to the heating element; and in response to the determination, activation of the heating element during a predefined lockout period may be prevented. The user device may be provided, in response to the determination, data indicative of the vaporizer session being completed. The vaporizer device may receive, from the user device, data indicative of the predefined lockout period being overridden; and in response to the receipt of the data indicative of the predefined lockout period being overridden, activation of the heating element may be allowed. Causing the vaporizer device to operate may include controlling, by the heater control circuitry, the heating element to operate at the selected temperature. Causing the vaporizer device to operate may be in response to a detection of a user drawing on a mouthpiece the vaporizer device. Providing the status data may be in response to a detection of a user drawing on a mouthpiece the vaporizer device. The user device may be provided information regarding the vaporizer device, where the information comprises a type of vaporizable material contained in the vaporizer device, predefined user settings, and/or predefined operational settings.

According to an aspect of the current subject matter, a method includes accessing, through operation of an application executing on one or more programmable processors, information regarding a vaporizer device; displaying, on a user interface generated on a display by the one or more programmable processors, one or more adjustable parameters for a vaporizer session of the vaporizer device, where the one or more adjustable parameters includes at least one of a session size and/or a temperature; receiving, by the one or more programmable processors, a selection of the one or more adjustable parameters; and providing, by the one or more programmable processors and to a controller of the vaporizer device, data indicative of the selection, where the data indicative of the selection includes operational settings to cause the vaporizer device to operate consistent with the selection.

According to an inter-related aspect, an apparatus includes at least one data processor and at least one memory storing instructions which, when executed by the at least one data processor, cause operations including accessing, through operation of an application executing on the at least one data processor, information regarding a vaporizer device; displaying, on a user interface generated on a display by the at least one data processor, one or more adjustable parameters for a vaporizer session of the vaporizer device, where the one or more adjustable parameters include at least one of a session size and/or a temperature; receiving, by the at least one data processor, a selection of the one or more adjustable parameters; and providing, by the at least one data processor and to a controller of the vaporizer device, data indicative of the selection, where the data indicative of the selection includes operational settings to cause the vaporizer device to operate consistent with the selection.

According to an inter-related aspect, a non-transitory computer readable medium is provided, the non-transitory computer readable medium storing instructions, which when executed by at least one data processor, result in operations including accessing, through operation of an application executing on the at least one data processor, information regarding a vaporizer device; displaying, on a user interface generated on a display by the at least one data processor, one or more adjustable parameters for a vaporizer session of the vaporizer device, where the one or more adjustable parameters includes at least one of a session size and/or a temperature; receiving, by the at least one data processor, a selection of the one or more adjustable parameters; and providing, by the at least one data processor and to a controller of the vaporizer device, data indicative of the selection, where the data indicative of the selection includes operational settings to cause the vaporizer device to operate consistent with the selection.

In some variations, one or more of the features disclosed herein including the following features can optionally be included in any feasible combination. The one or more adjustable parameters may include the session size, where the display of the session size includes a dropdown menu including a plurality of selectable session size options for the vaporizer session, and where the selection of the session size includes selecting, via user interaction, one of the plurality of selectable session size options. The one or more adjustable parameters may include the temperature, where the display of the temperature includes a slideable selection bar including a slideable icon, and where the selection of the temperature includes positioning, via user interaction, the slideable icon at a temperature point along the slideable selection bar.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 5A-FIG. 5H illustrate features of exemplary user interfaces that may be presented by an application for selecting a particular session, in accordance with some example implementations;

FIG. 6A-FIG. 6J illustrate features of exemplary user interfaces that may be presented by an application for selecting a temperature, in accordance with some example implementations;

When practical, similar reference numbers denote similar structures, features, or elements.

DETAILED DESCRIPTION

Figure 1A:
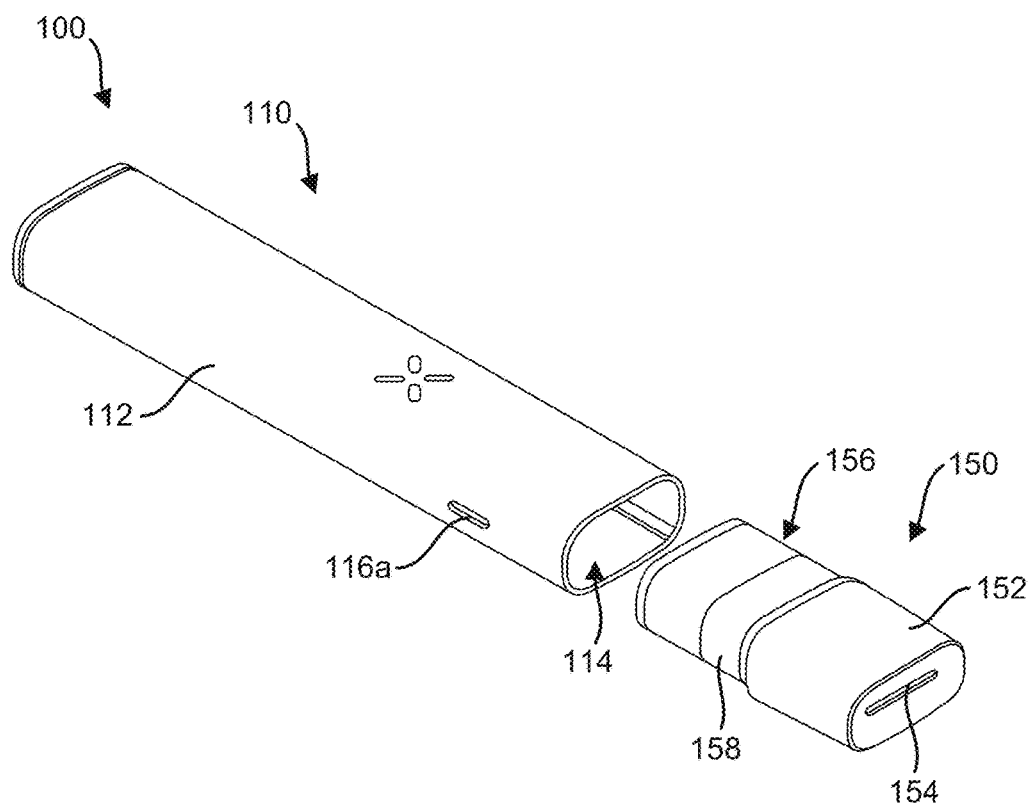
FIG. 1A-FIG. 1F illustrate features of a vaporizer device including a vaporizer body and a cartridge consistent with implementations of the current subject matter.

Aspects of the current subject matter relate to vaporizer devices configured to allow for user control of an amount of vapor consumed. Before providing additional details regarding aspects of user control of an amount of vapor consumed, the following provides a description of some examples of vaporizer devices including a vaporizer body and a cartridge. The following descriptions are meant to be exemplary, and aspects related to providing for user control of an amount of vapor consumed consistent with the current subject matter are not limited to the example vaporizer devices described herein.

Implementations of the current subject matter include devices relating to vaporizing of one or more materials for inhalation by a user. The term "vaporizer" may be used generically in the following description and may refer to a vaporizer device, such as an electronic vaporizer. Vaporizers consistent with the current subject matter may be referred to by various terms such as inhalable aerosol devices, aerosolizers, vaporization devices, electronic vaping devices, electronic vaporizers, vape pens, etc. Examples of vaporizers consistent with implementations of the current subject matter include electronic vaporizers, electronic cigarettes, e-cigarettes, or the like. In general, such vaporizers are often portable, hand-held devices that heat a vaporizable material to provide an inhalable dose of the material. The vaporizer may include a heater configured to heat a vaporizable material which results in the production of one or more gas-phase components of the vaporizable material. A vaporizable material may include liquid and/or oil-type plant materials, or a semi-solid like a wax, or plant material such as leaves or flowers, either raw or processed. The gas-phase components of the vaporizable material may condense after being vaporized such that an aerosol is formed in a flowing air stream that is deliverable for inhalation by a user. The vaporizers may, in some implementations of the current subject matter, be particularly adapted for use with an oil-based vaporizable material, such as cannabis-derived oils although other types of vaporizable materials may be used as well.

One or more features of the current subject matter, including one or more of a cartridge (also referred to as a vaporizer cartridge or pod) and a reusable vaporizer device body (also referred to as a vaporizer device base, a body, a vaporizer body, or a base), may be employed with a suitable vaporizable material (where suitable refers in this context to being usable with a device whose properties, settings, etc. are configured or configurable to be compatible for use with the vaporizable material). The vaporizable material may include one or more liquids, such as oils, extracts, aqueous or other solutions, etc., of one or more substances that may be desirably provided in the form of an inhalable aerosol. The cartridge may be inserted into the vaporizer body, and then the vaporizable material heated which results in the inhalable aerosol.

Figure 1B:
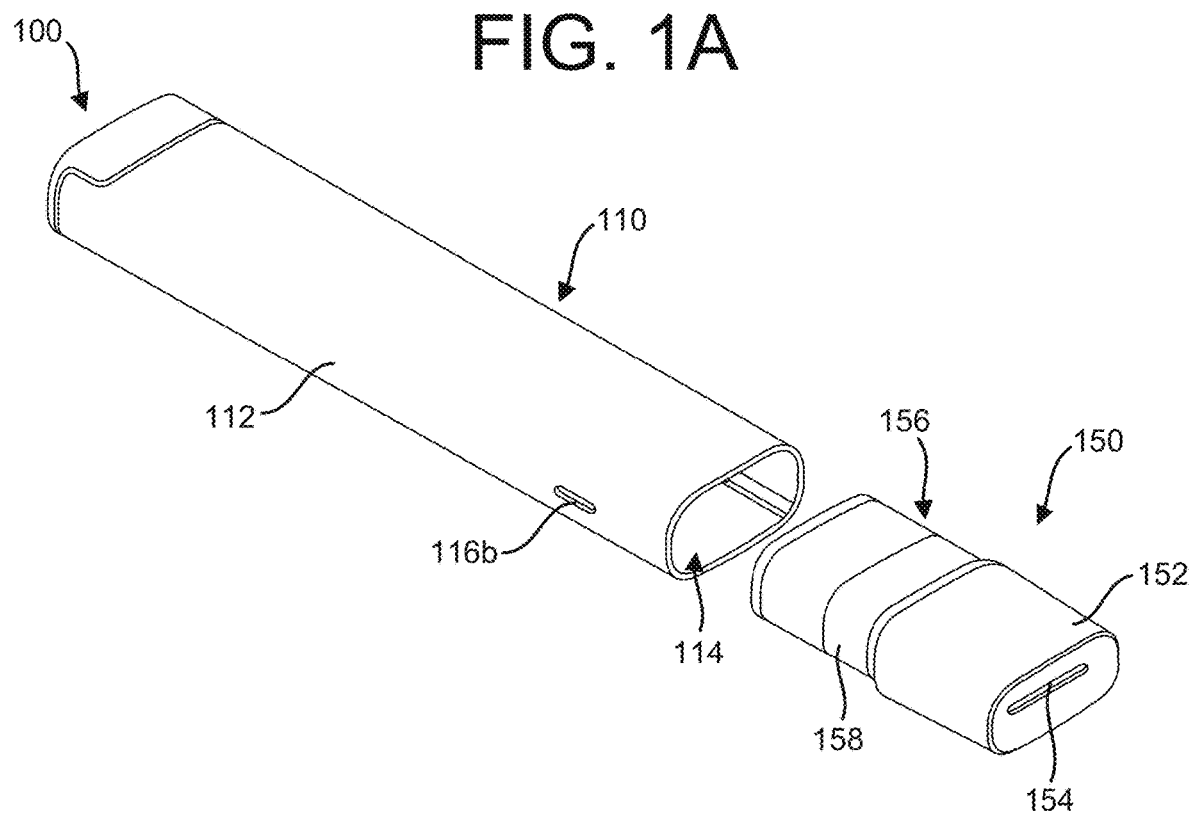
Figure 1C:
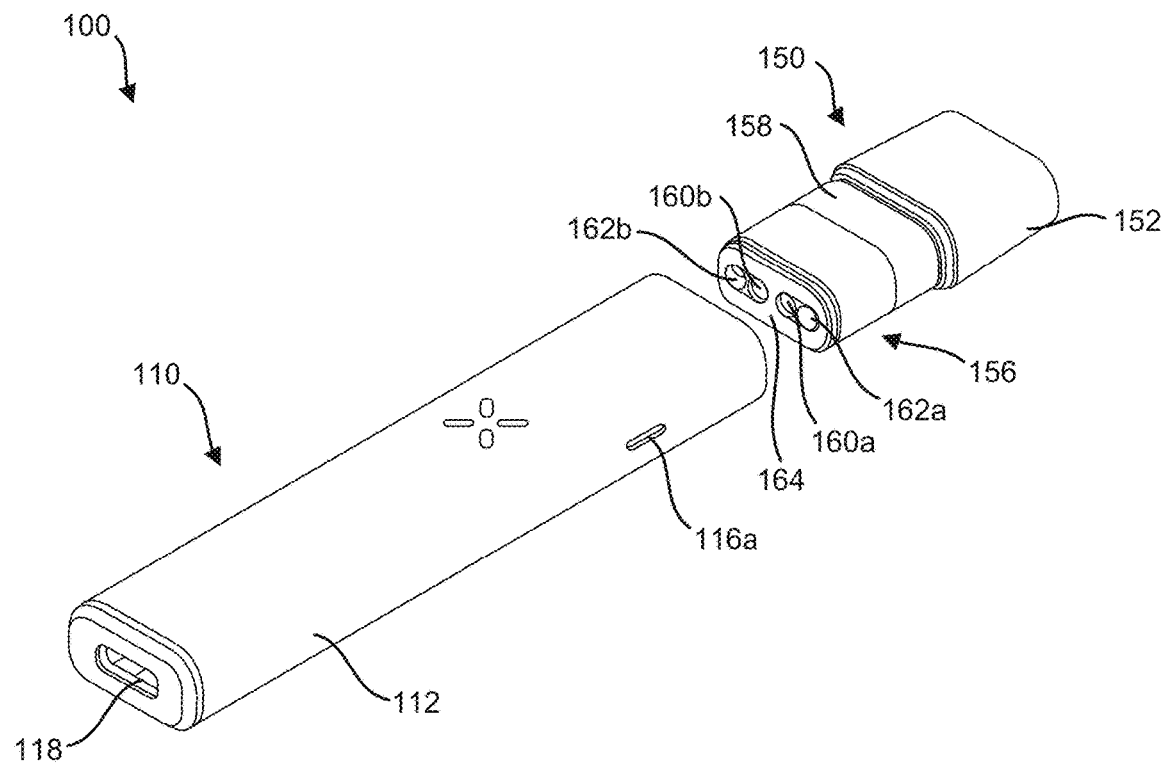
Figure 1D:
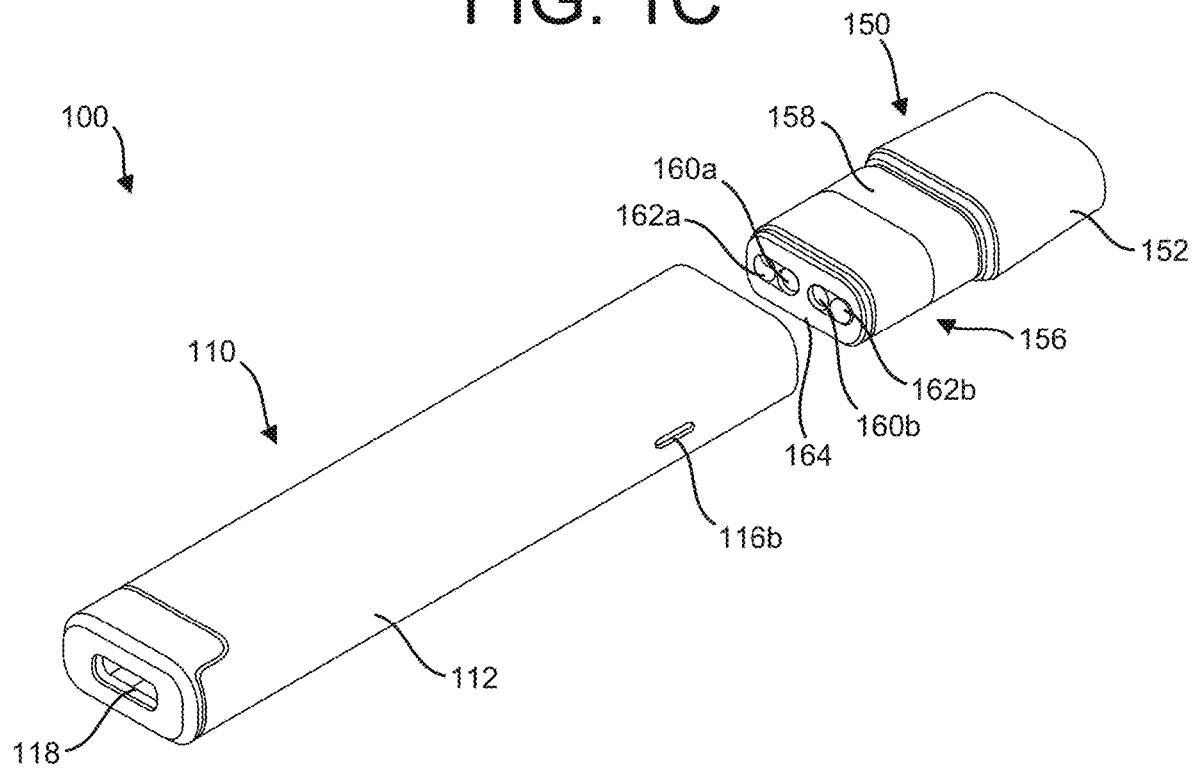
Figure 1E:
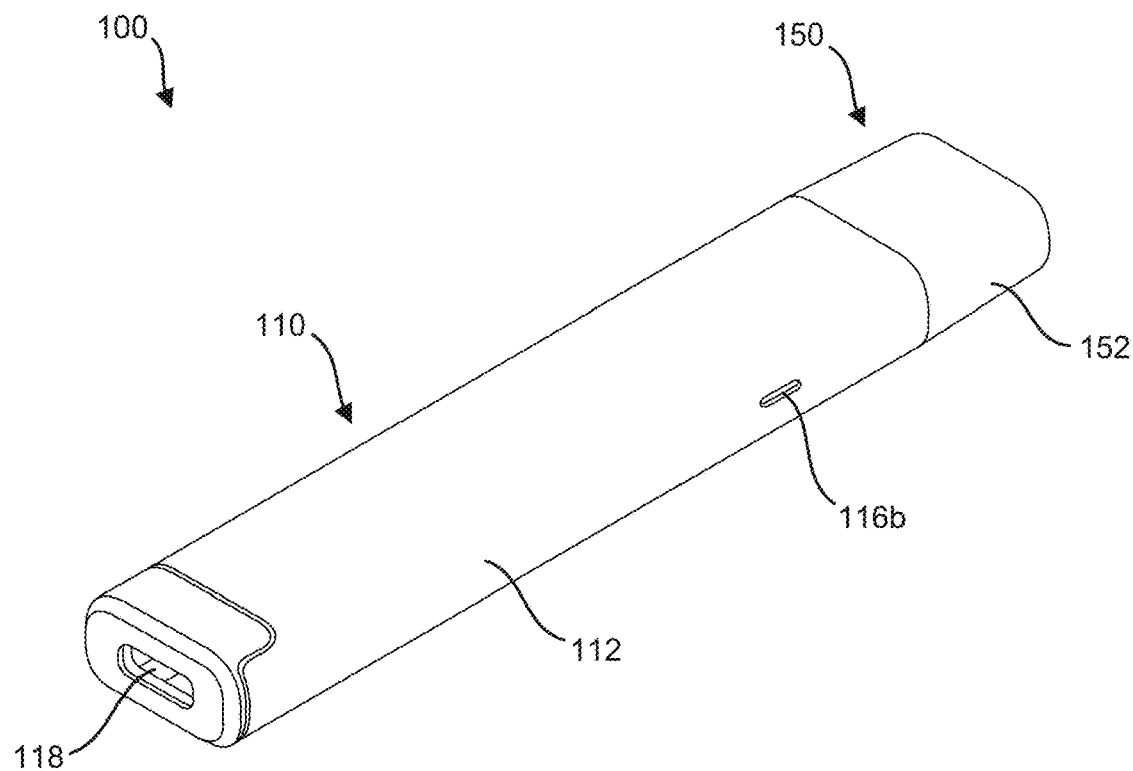
Figure 1F:
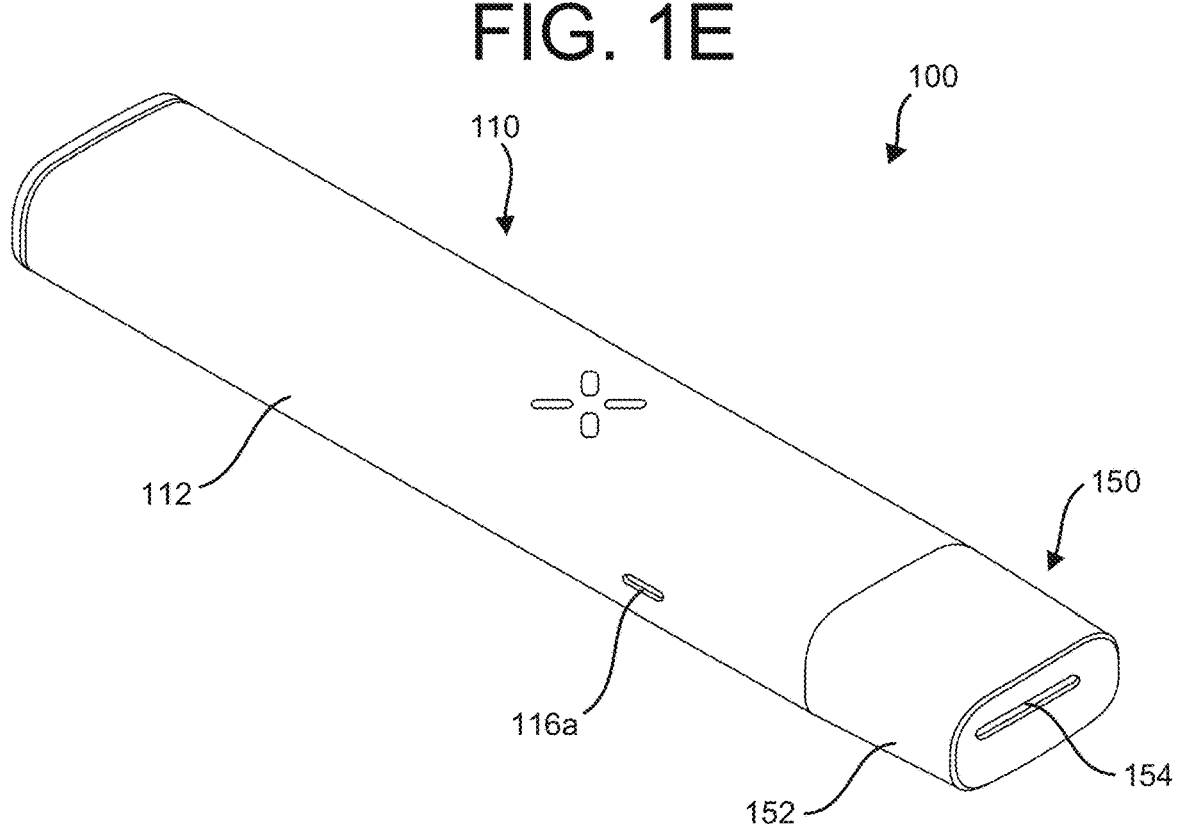

FIG. 1A-FIG. 1F illustrates features of a vaporizer device 100 including a vaporizer body 110 and a cartridge 150 consistent with implementations of the current subject matter. FIG. 1A is a bottom perspective view, and FIG. 1B is a top perspective view of the vaporizer device 100 with the cartridge 150 separated from a cartridge receptacle 114 on the vaporizer body 110. Both of the views in FIG. 1A and FIG. 1B are shown looking towards a mouthpiece 152 of the cartridge 150. FIG. 1C is a bottom perspective view, and FIG. 1D is a top perspective view of the vaporizer device with the cartridge 150 separated from the cartridge receptacle 114 of the vaporizer body 110. FIG. 1C and FIG. 1D are shown looking toward the distal end of the vaporizer body 110. FIG. 1E is top perspective view, and FIG. 1F is a bottom perspective view of the vaporizer device 100 with the cartridge 150 engaged for use with the vaporizer body 110.

As shown in FIG. 1A-FIG. 1D, the cartridge 150 includes, at the proximal end, a mouthpiece 152 that is attached over a cartridge body 156 that forms a reservoir or tank 158 that holds a vaporizable material. The cartridge body 156 may be transparent, translucent, opaque, or a combination thereof. The mouthpiece 152 may include one or more openings 154 (see FIG. 1A, FIG. 1B, FIG. 1F) at the proximal end out of which vapor may be inhaled, by drawing breath through the vaporizer device 100. The distal end of the cartridge body 156 may couple to and be secured to the vaporizer body 110 within the cartridge receptacle 114 of the vaporizer body 110. Power pin receptacles 160a,b (see FIG. 1C, FIG. 1D) of the cartridge 150 mate with respective power pins or contacts 122a,b (see, for example, FIG. 2) of the vaporizer body 110 that extend into the cartridge receptacle 114. The cartridge 150 also includes air flow inlets 162a,b on the distal end of the cartridge body 156.

A tag 164, such as a data tag, a near-field communication (NFC) tag, or other type of wireless transceiver or communication tag, may be positioned on at least a portion of the distal end of the cartridge body 156. As shown in FIG. 1C and FIG. 1D, the tag 164 may substantially surround the power pin receptacles 160a,b and the air flow inlets 162a,b, although other configurations of the tag 164 may be implemented as well. For example, the tag 164 may be positioned between the power pin receptacle 160a and the power pin receptacle 160b, or the tag 164 may be shaped as a circle, partial circle, oval, partial oval, or any polygonal shape encircling or partially encircling the power pin receptacles 160a,b and the air flow inlets 162a,b or a portion thereof.

In the example of FIG. 1A, the vaporizer body 110 has an outer shell or cover 112 that may be made of various types of materials, including for example aluminum (e.g., AL6063), stainless steel, glass, ceramic, titanium, plastic (e.g., Acrylonitrile Butadiene Styrene (ABS), Nylon, Polycarbonate (PC), Polyethersulfone (PESU), and the like), fiberglass, carbon fiber, and any hard, durable material. The proximal end of the vaporizer body 110 includes an opening forming the cartridge receptacle 114, and the distal end of the vaporizer body 110 includes a connection 118, such as, for example, a universal serial bus Type C (USB-C) connection and/or the like. The cartridge receptacle 114 portion of the vaporizer body 110 includes one or more openings (air inlets) 116a,b that extend through the outer shell 112 to allow airflow therein, as described in more detail below. The vaporizer body 110 as shown has an elongated, flattened tubular shape that is curvature-continuous, although the vaporizer body 110 is not limited to such a shape. The vaporizer body 110 may take the form of other shapes, such as, for example, a rectangular box, a cylinder, and the like.

The cartridge 150 may fit within the cartridge receptacle 114 by a friction fit, snap fit, and/or other types of secure connection. The cartridge 150 may have a rim, ridge, protrusion, and/or the like for engaging a complimentary portion of the vaporizer body 110. While fitted within the cartridge receptacle 114, the cartridge 150 may be held securely within but still allow for being easily withdrawn to remove the cartridge 150.

Although FIG. 1A-FIG. 1F illustrate a certain configuration of the vaporizer device 100, the vaporizer device 100 may take other configurations as well.

Figure 2:
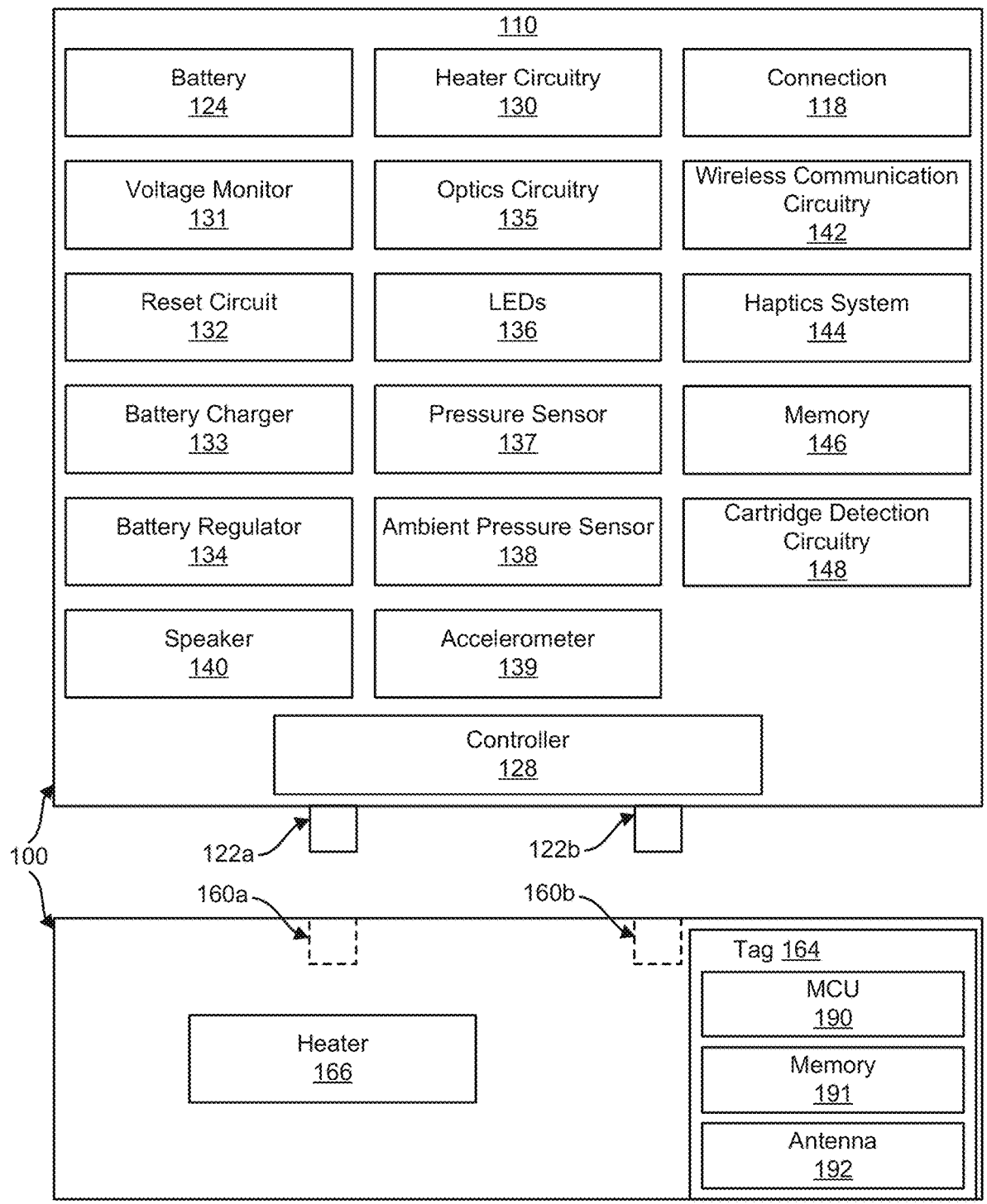
FIG. 2 is a schematic block diagram illustrating features of a vaporizer device having a cartridge and a vaporizer body consistent with implementations of the current subject matter.

FIG. 2 is a schematic block diagram illustrating components of the vaporizer device 100 having the cartridge 150 and the vaporizer body 110 consistent with implementations of the current subject matter. Included in the vaporizer body 110 is a controller 128 that includes at least one processor and/or at least one memory configured to control and manage various operations among the components of the vaporizer device 100 described herein.

Heater control circuitry 130 of the vaporizer body 110 controls a heater 166 of the cartridge 150. The heater 166 may generate heat to provide vaporization of the vaporizable material. For example, the heater 166 may include a heating coil (e.g., a resistive heater) in thermal contact with a wick which absorbs the vaporizable material, as described in further detail below.

A battery 124 is included in the vaporizer body 110, and the controller 128 may control and/or communicate with a voltage monitor 131 which includes circuitry configured to monitor the battery voltage, a reset circuit 132 configured to reset (e.g., shut down the vaporizer device 100 and/or restart the vaporizer device 100 in a certain state), a battery charger 133, and a battery regulator 134 (which may regulate the battery output, regulate charging/discharging of the battery, and provide alerts to indicate when the battery charge is low, etc.).

The power pins 122a,b of the vaporizer body 110 engage the complementary power pin receptacles 160a,b of the cartridge 150 when the cartridge 150 is engaged with the vaporizer body 110. Alternatively, power pins may be part of the cartridge 150 for engaging complementary power pin receptacles of the vaporizer body 110. The engagement allows for the transfer of energy from an internal power source (e.g., the battery 124) to the heater 166 in the cartridge 150. The controller 128 may regulate the power flow (e.g., an amount or current and/or a voltage amount) to control a temperature at which the heater 166 heats the vaporizable material contained in the reservoir 158. According to implementations of the current subject matter, a variety of electrical connectors other than a pogo-pin and complementary pin receptacle configuration may be used to electrically connect the vaporizer body 110 and the cartridge 150, such as for example, a plug and socket connector.

The controller 128 may control and/or communicate with optics circuitry 135 (which controls and/or communicates with one or more displays such as LEDs 136 which may provide user interface output indications), a pressure sensor 137, an ambient pressure sensor 138, an accelerometer 139, and/or a speaker 140 configured to generate sound or other feedback to a user.

The pressure sensor 137 may be configured to sense a user drawing (i.e., inhaling) on the mouthpiece 152 and activate the heater control circuitry 130 of the vaporizer body 110 to accordingly control the heater 166 of the cartridge 150. In this way, the amount of current supplied to the heater 166 may be varied according the user's draw (e.g., additional current may be supplied during a draw, but reduced when there is not a draw taking place). The ambient pressure sensor 138 may be included for atmospheric reference to reduce sensitivity to ambient pressure changes and may be utilized to reduce false positives potentially detected by the pressure sensor 137 when measuring draws from the mouthpiece 152.

The accelerometer 139 (and/or other motion sensors, capacitive sensors, flow sensors, strain gauge(s), or the like)

may be used to detect user handling and interaction, for example, to detect movement of the vaporizer body 110 (such as, for example, tapping, rolling, and/or any other deliberate movement associated with the vaporizer body 110). The detected movements may be interpreted by the controller 128 as one or more predefined user commands. For example, one particular movement may be a user command to gradually increase the temperature of the heater 166 as the user intends to begin using the vaporizer device 100.

The vaporizer body 110, as shown in FIG. 2, includes wireless communication circuitry 142 that is connected to and/or controlled by the controller 128. The wireless communication circuitry 142 may include a near-field communication (NFC) antenna that is configured to read from and/or write to the tag 164 of the cartridge 150. Alternatively or additionally, the wireless communication circuitry 142 may be configured to automatically detect the cartridge 150 as it is being inserted into the vaporizer body 110. In some implementations, data exchanges between the vaporizer body 110 and the cartridge 150 take place over NFC.

The wireless communication circuitry 142 may include additional components including circuitry for other communication technology modes, such as Bluetooth circuitry, Bluetooth Low Energy circuitry, Wi-Fi circuitry, cellular (e.g., LTE, 4G, and/or 5G) circuitry, and associated circuitry (e.g., control circuitry), for communication with other devices. For example, the vaporizer body 110 may be configured to wirelessly communicate with a remote processor (e.g., a smartphone, a tablet, a computer, wearable electronics, a cloud server, and/or processor based devices) through the wireless communication circuitry 142, and the vaporizer body 110 may through this communication receive information including control information (e.g., for setting temperature, resetting a dose counter, etc.) from and/or transmit output information (e.g., dose information, operational information, error information, temperature setting information, charge/battery information, etc.) to one or more of the remote processors.

The tag 164 may be a type of wireless transceiver and may include a microcontroller unit (MCU) 190, a memory 191, and an antenna 192 (e.g., an NFC antenna) to perform the various functionalities described below with further reference to FIG. 3. NFC tag 164 may be, for example, a 1 Kbit or a 2 Kbit tag that is of type ISO/IEC 15693. NFC tags with other specifications may also be used. The tag 164 may be implemented as active NFC, enabling reading and/or writing information via NFC with other NFC compatible devices including a remote processor, another vaporizer device, and/or wireless communication circuitry 142. Alternatively, the tag 164 may be implemented using passive NFC technology, in which case other NFC compatible devices (e.g., a remote processor, another vaporizer device, and/or wireless communication circuitry 142) may only be able to read information from the tag 164.

The vaporizer body 110 may include a haptics system 144, such as an actuator, a linear resonant actuator (LRA), an eccentric rotating mass (ERM) motor, or the like that provide haptic feedback such as a vibration as a "find my device" feature or as a control or other type of user feedback signal. For example, using an app running on a user device (such as, for example, a user device 305 shown in FIG. 3), a user may indicate that he/she cannot locate his/her vaporizer device 100. Through communication via the wireless communication circuitry 142, the controller 128 sends a signal to the haptics system 144, instructing the haptics system 144 to provide haptic feedback (e.g., a vibration).

The controller 128 may additionally or alternatively provide a signal to the speaker 140 to emit a sound or series of sounds. The haptics system 144 and/or speaker 140 may also provide control and usage feedback to the user of the vaporizer device 100; for example, providing haptic and/or audio feedback when a particular amount of a vaporizable material has been used or when a period of time since last use has elapsed. Alternatively or additionally, haptic and/or audio feedback may be provided as a user cycles through various settings of the vaporizer device 100. Alternatively or additionally, the haptics system 144 and/or speaker 140 may signal when a certain amount of battery power is left (e.g., a low battery warning and recharge needed warning) and/or when a certain amount of vaporizable material remains (e.g., a low vaporizable material warning and/or time to replace the cartridge 150). Alternatively or additionally, the haptics system 144 and/or speaker 140 may also provide usage feedback and/or control of the configuration of the vaporizer device 100 (e.g., allowing the change of a configuration, such as target heating rate, heating rate, etc.).

The vaporizer body 110 may include circuitry for sensing/detecting when a cartridge 150 is connected and/or removed from the vaporizer body 110. For example, cartridge-detection circuitry 148 may determine when the cartridge 150 is connected to the vaporizer body 110 based on an electrical state of the power pins 122a,b within the cartridge receptacle 114. For example, when the cartridge 150 is present, there may be a certain voltage, current, and/or resistance associated with the power pins 122a,b, when compared to when the cartridge 150 is not present. Alternatively or additionally, the tag 164 may also be used to detect when the cartridge 150 is connected to the vaporizer body 110.

The vaporizer body 110 also includes the connection (e.g., USB-C connection, micro-USB connection, and/or other types of connectors) 118 for coupling the vaporizer body 110 to a charger to enable charging the internal battery 124. Alternatively or additionally, electrical inductive charging (also referred to as wireless charging) may be used, in which case the vaporizer body 110 would include inductive charging circuitry to enable charging. The connection 118 at FIG. 2 may also be used for a data connection between a computing device and the controller 128, which may facilitate development activities such as, for example, programming and debugging, for example.

The vaporizer body 110 may also include a memory 146 that is part of the controller 128 or is in communication with the controller 128. The memory 146 may include volatile and/or non-volatile memory or provide data storage. In some implementations, the memory 146 may include 8 Mbit of flash memory, although the memory is not limited to this and other types of memory may be implemented as well.

Figure 3:
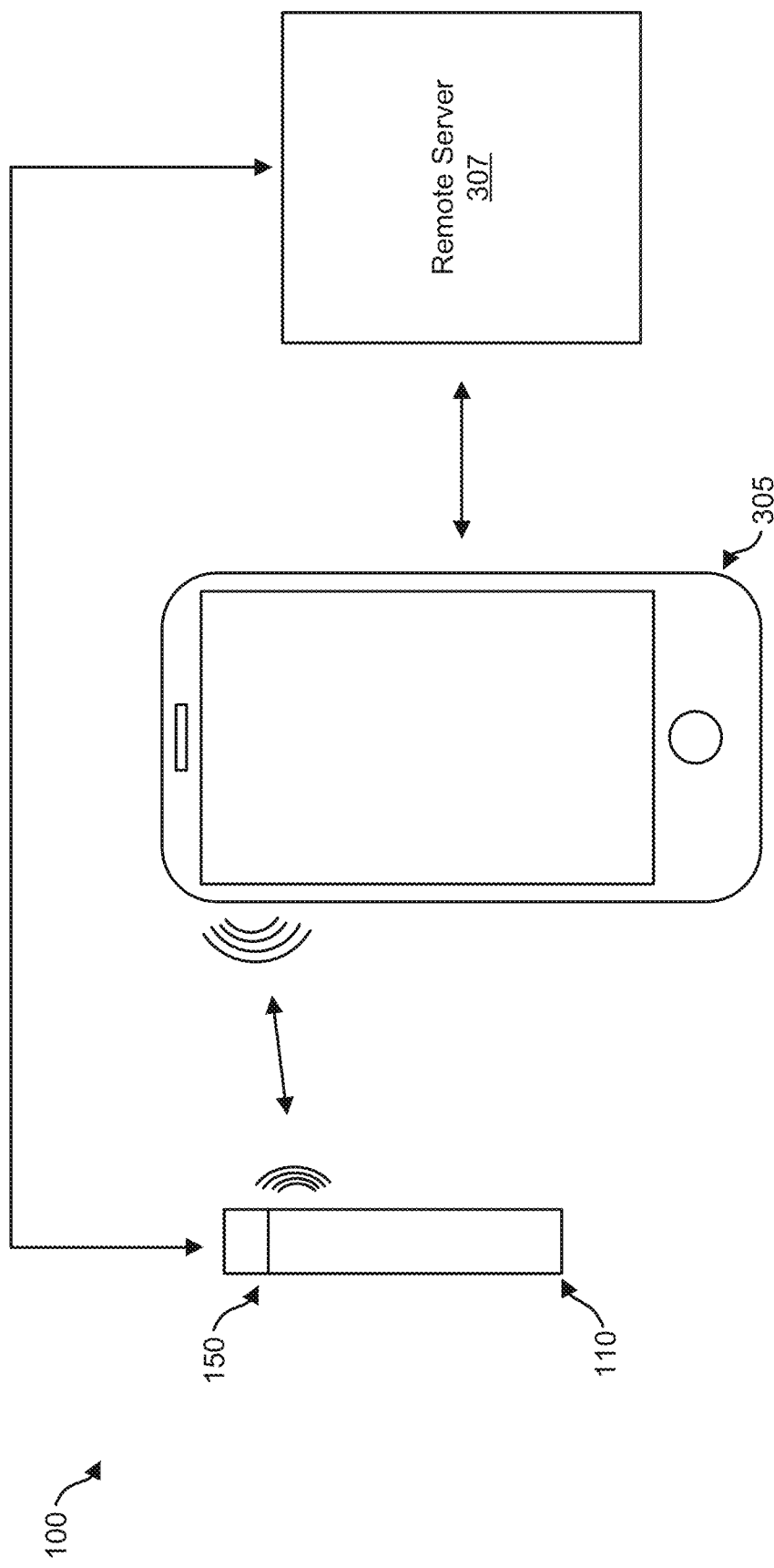
FIG. 3 illustrates communication between a vaporizer device, a user device, and a server consistent with implementations of the current subject matter.

FIG. 3 illustrates communication between the vaporizer device 100 (including the vaporizer body 110 and the cartridge 150), the user device 305 (e.g., a smartphone, tablet, laptop, and/or the like), and a remote server 307 (e.g., a server coupled to a network, a cloud server coupled to the Internet, and/or the like) consistent with implementations of the current subject matter. The user device 305 wirelessly communicates with the vaporizer device 100. A remote server 307 may communicate directly with the vaporizer device 100 or through the user device 305. The vaporizer body 110 may communicate with the user device 305 and/or the remote server 307 through the wireless communication circuitry 142. In some implementations, the cartridge 150 may establish through the tag 164 communication with the vaporizer body 110, the user device 305, and/or the remote server 307.

An application software ("app") running on at least one of the remote processors (the user device 305 and/or the remote server 307) may be configured to control operational aspects of the vaporizer device 100 and receive information relating to operation of the vaporizer device 100. For example, the app may provide a user with capabilities to input or set desired properties or effects, such as, for example, a particular temperature or desired dose, which is then communicated to the controller 128 of the vaporizer body 110 through the wireless communication circuitry 142. The app may also provide a user with functionality to select one or more sets of suggested properties or effects that may be based on the particular type of vaporizable material in the cartridge 150. For example, the app may allow adjusting heating based on the type of vaporizable material, the user's (of the vaporizer device 100) preferences or desired experience, and/or the like.

In some implementations, the app may provide to the remote server 307 and/or the user device 305 information related to the vaporizer device 100. The provided data may include information identifying the cartridge 150 (e.g., pod ID), information identifying the composition of the vaporizable material in the cartridge 150 (e.g., batch ID), information identifying the vendor of the cartridge 150 (e.g., vendor ID), usage information, such as puffs taken (puff count), time of day of the puff, an amount of energy (e.g., joules) applied to the vaporizable material, an amount of the vaporizable material in the cartridge 150 (e.g., weight, etc.) currently or when initially filled, user experience information (e.g., user's perceived experience caused by a puff, such as calm, alert, like, dislike, etc.), and/or cartridge configuration (e.g., a target heater temperature to achieve vaporization, a ramp rate to the target temperate, etc.).

The app of the user device 305 may allow a user to perform a hard-reset of the vaporizer device 100. For example, a user may indicate through the app that the vaporizer device 100 should be reset, which may cause the vaporizer device 100 to shut down, which may be performed by the reset circuit 132. Following shut-down, the vaporizer device 100 may enter a standby mode or may resume operation, depending upon a variety of factors, such as for example the reason (if known) for the reset. The input and/or user selections may act as control signals for the controller 128 to perform a corresponding function (e.g., reach and hold a defined temperature, provide a certain dose, reduce heat after a certain time period, reset, etc.). Likewise, the controller 128 may transmit information, through the wireless communication circuitry 142, to one of the remote processors for display via the app. For example, a summary of use of the vaporizer device 100 throughout a day may be tracked and sent to the user device 305.

Data read from the tag 164 from the wireless communication circuitry 142 of the vaporizer body 110 may be transferred to one or more of the remote processors (e.g., the user device 305 and/or the remote server 307) to which it is connected, which allows for the app running on the one or more processors to access and utilize the read data for a variety of purposes. For example, the read data relating to the cartridge 150 may be used for providing recommended temperatures, session control, usage tracking, and/or assembly information.

The cartridge 150 may also communicate directly, through the tag 164, with other devices. This enables data relating to the cartridge 150 to be written to/read from the tag 164, without interfacing with the vaporizer body 110. The tag 164 thus allows for identifying information (e.g., pod ID, batch ID, etc.) related to the cartridge 150 to be associated with the cartridge 150 by one or more remote processors. For example, when the cartridge 150 is filled with a certain type of vaporizable material, this information may be transmitted to the tag 164 by filling equipment. Then, the vaporizer body 110 is able to obtain this information from the tag 164 (e.g., via circuity 142 at the vaporizer body 110) to identify the vaporizable material currently being used and accordingly adjust the controller 128 based on, for example, user-defined criteria or pre-set parameters associated with the particular type of vaporizable material (set by a manufacturer or as determined based upon user experiences/feedback aggregated from other users). For example, a user may establish (via the app) a set of criteria relating to desired effects for or usage of one or more types of vaporizable materials. When a certain vaporizable material is identified, based on communication via the tag 164, the controller 128 may accordingly adopt the established set of criteria, which may include, for example, temperature and dose, for that particular vaporizable material.

Other information related to the cartridge 150 may be transmitted to and stored on the tag 164, such as information relating to components of the cartridge 150, for example heating components. The controller 128 of the vaporizer body 110 may use this information to control a usage session for a user. A manufacturer of the cartridge 150 may thus transmit manufacturing information to the tag 164 for storage for subsequent use by the controller 128 or other remote processors (e.g., the user device 305 and/or the remote server 307).

Consistent with implementations of the current subject matter, the vaporizable material used with the vaporizer device may be provided within the cartridge. The vaporizer device may be a cartridge-using vaporizer device, a cartridge-less vaporizer device, or a multi-use vaporizer device capable of use with or without a cartridge. For example, a multi-use vaporizer device may include a heating chamber (e.g., an oven) configured to receive the vaporizable material directly in the heating chamber and also configured to receive the cartridge having a reservoir or the like for holding the vaporizable material. In various implementations, the vaporizer device may be configured for use with liquid vaporizable material (e.g., a carrier solution in which an active and/or inactive ingredient(s) are suspended or held in solution or a liquid form of the vaporizable material itself) or solid vaporizable material. Solid vaporizable material may include a plant material that emits some part of the plant material as the vaporizable material (e.g., such that some part of the plant material remains as waste after the vaporizable material is emitted for inhalation by a user) or optionally may be a solid form of the vaporizable material itself such that all of the solid material may eventually be vaporized for inhalation. Liquid vaporizable material may likewise be capable of being completely vaporized or may include some part of the liquid material that remains after all of the material suitable for inhalation has been consumed.

Figure 4:
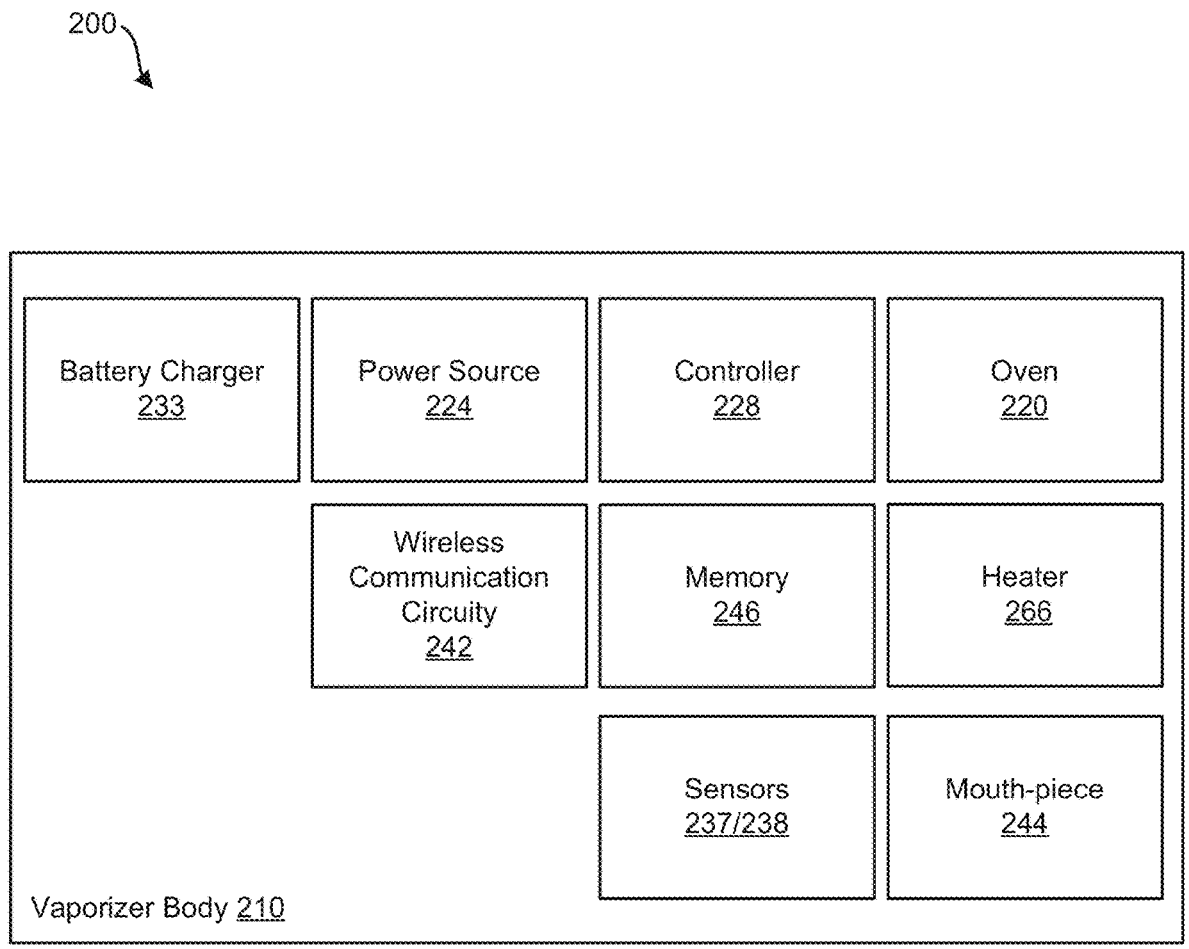
FIG. 4 is a schematic block diagram illustrating features of another vaporizer device consistent with implementations of the current subject matter.

FIG. 4 is a schematic block diagram illustrating features of another vaporizer device 200 consistent with implementations of the current subject matter. The vaporizer device 200 does not require use of a cartridge (but may still optionally accept a cartridge), but may instead use a loose-leaf material. The vaporizer device 200 in FIG. 4 includes an oven 220 (e.g., vaporization chamber) in which loose vaporizable material may be placed in an oven 220. Many of the same elements present in the vaporizer device 100 using the cartridge 150 shown in FIG. 1A-FIG. 1F and FIG. 2 may also be included as part of the vaporizer device 200. For example, the vaporizer device 200 may include a vaporizer body 210 with controller 228, wireless communication circuitry 242, and/or memory 246. A power source 224 (e.g., battery, capacitor, etc.) may be charged by a battery charger 233 (and may include charging control circuitry, not shown). The vaporizer device 200 may also include one or more sensors 237, 238. In addition, the vaporizer device 200 may include one or more heaters 266 that heat the oven 220. The heater 266 may be controlled using the resistance of the heater 266 to determine the temperature of the heater, e.g., by using the temperature coefficient of resistivity for the heater 266. Convection heating methods may be used. A mouthpiece 244 may also be included.

The vaporizer device consistent with implementations of the current subject matter may be configured to facilitate social interaction through the vaporizer device. For example, the vaporizer device may be configured to share usage information with others, such as third parties including health care providers, etc., for better prescription and administration of medical treatment. The vaporizer device may also be configured to communicate with non-medical third parties (e.g., friends, colleagues, etc.), and with unknown third parties (making some or all information publically available). In some implementations, the vaporizer device described herein, either by itself or in communication with one or more communications devices that are part of a system, may identify and provide information about the operation, status, or user input from the vaporizer device to a public or private network.

Software, firmware, or hardware that is separate or separable from the vaporizer device and that wirelessly communicates with the vaporizer device may be provided as described with respect to FIG. 3. For example, applications ("apps") may be executed on a processor of a portable and/or wearable device, including smartphones, smartwatches, and the like, which may be referred to as a personal digital device, a user device, or optionally just a device (e.g., user device 305 in FIG. 3) that is part of a connected system. These digital devices may provide an interface for the user to engage and interact with functions related to the vaporizer device, including communication of data to and from the vaporizer device to the digital device or the like and/or additional third party processor (e.g., servers such as the remote server 307 in FIG. 3). For example, a user may control some aspects of the vaporizer device (temperature, session size, etc.) and/or data transmission and data receiving to and from the vaporizer device, optionally over a wireless communication channel between first communication hardware of the digital device and second communication hardware of the vaporizer device. Data may be communicated in response to one or more actions of the user (e.g., including interactions with a user interface displayed on the device), and/or as a background operation such that the user does not have to initiate or authorize the data communication process.

User interfaces may be deployed on the digital device and may aid the user in operating the vaporizer device. For example, the user interface operating on the digital device may include icons and text elements that may inform the user of various ways that vaporizer settings may be adjusted or configured by the user. In this manner (or in others consistent with the current subject matter) information about the vaporizer device may be presented using the user interface displayed by the digital device. Icons and/or text elements may be provided to allow the user to see information regarding one or more statuses of the vaporizer device, such as battery information (charge remaining, draws remaining, time to charge, charging, etc.), cartridge status (e.g., type of cartridge and vaporizable material, fill status of cartridge, etc.), and other device statuses or information. Icons and/or text elements may be provided to allow the user to update internal software (a.k.a., firmware) in the vaporizer device. Icons and text elements may be provided to allow the user to set security and/or authorization features of the vaporizer device, such as setting a PIN code to activate the vaporizer device or the use of personal biometric information as a way of authentication. Icons and text elements may be provided to allow the user to configure foreground data sharing and related settings.

The vaporizer device may perform onboard data gathering, data analysis, and/or data transmission methods. As mentioned, the vaporizer device having wired or wireless communication capability may interface with digital consumer technology products such as smart phones, tablet computers, laptop/netbook/desktop computers, wearable wireless technologies such as "smart watches," and other wearable technology such as Google "Glass," or similar through the use of programming, software, firmware, GUI, wireless communication, wired communication, and/or software commonly referred to as application(s) or "apps." A wired communication connection may be used to interface the vaporizer device to digital consumer technology products for the purpose of the transmission and exchange of data to/from the vaporizer device from/to the digital consumer technology products (and thereby also interfacing with apps running on the digital consumer technology products). A wireless communication connection may be used to interface the vaporizer device to digital consumer technology products for the transmission and exchange of data to/from the vaporizer device from/to the digital wireless interface. The vaporizer device may use a wireless interface that includes one or more of an infrared (IR) transmitter, a Bluetooth interface, an 802.11 specified interface, and/or communications with a cellular telephone network in order to communicate with consumer technology.

The vaporizer device and/or the user device as defined above may be used for any of one or more functions, such as controlling dosing (e.g., dose monitoring, dose setting, dose limiting, user tracking, etc.), controlling sessioning (e.g., session monitoring, session setting, session limiting, user tracking, etc.), obtaining locational information (e.g., location of other users, retailer/commercial venue locations, vaping locations, relative or absolute location of the vaporizer device itself, etc.), vaporizer device personalization (e.g., naming the vaporizer device, locking and/or password protecting the vaporizer device, adjusting one or more parental controls, associating the vaporizer device with a user group, registering the vaporizer device with a manufacturer or warranty maintenance organization, etc.), engaging in social activities (e.g., games, social media communications, interacting with one or more groups, etc.) with other users, or the like. The terms "sessioning", "session", "vaporizer session," "vapor session," or "vaporization session" are used generically in the following description and claims to refer to a period devoted to the use of the vaporizer device. The period may include a time period, number of doses, amount of vaporizable material, and/or the like.

As described above, the vaporizer device 100 and/or the user device 305 that is part of a vaporizer system as defined above may include a user interface (e.g., including an app or application software) that may be executed on the user device 305 in communication, which may be configured to determine, display, enforce, and/or meter dosing.

In some implementations of the current subject matter, dose may be calculated over a time period that is divided into a plurality of sequential time intervals (which may be referred to as partial dose intervals) to determine the partial dose or mass of vapor produced during each partial dose interval. Each partial dose may be based on power applied before or at the start of each partial dose interval and the temperature at the start and at the end of each partial dose interval. The dose interval values may be summed over the entire time period to determine the overall dose of vapor generated, which may then be correlated to a dose of an active ingredient in the vaporizable material. In some implementations, the total mass vaporized may be predicted or determined based upon equation 1:

$$\Delta m_{vap,cumulative} = \Sigma_{i=1}^{i=n} a[P_i - b(T_i - T_{i-1}) - cT_i] \quad \text{(equation 1)},$$

where $\Delta m_{vap,cumulative}$ is the total mass vaporized during sampling intervals i=1 to i=n, each interval being of a fixed time increment; $P_i$ is power supplied during interval i; a, b, and c are constants; $T_i$ is temperature reading for interval i; $T_{i-1}$ is temperature reading for interval immediately before the current interval (i−1 immediately prior to interval i). Note that in some variations, the temperature may be temperature relative to room (or starting) temperature and may be expressed as $T_i'$ (e.g., $T_i'$, $T_{i-1}'$, etc.) An alternative expression of this relationship may be described as:

$$\Delta m_{vap,cumulative} = \Sigma_{i=1}^{i=n} [aP_i - dT_i - eT_{i-1}] \quad \text{(equation 2)}.$$

In this example, different coefficient may be used (e.g., d, e); this expression may be more simply implemented using a microcontroller than equation 1, as it has fewer arithmetic functions required, though it is mathematically equivalent. The coefficients a, b, and c may reflect physical constants whose values may be determined experimentally and may vary depending on the vaporizable material used. For example, the coefficients a, b, and c may depend upon the latent heat and the specific heat of the material being vaporized. The coefficients may further depend upon the overall mass of the system that needs to be heated (such as the liquid material and the heater, e.g., a wick and coil). The coefficients may be determined empirically or based on theoretical values knowing the dimensions and material properties of the vaporizable material and heater, for example.

Consistent with implementations of the current subject matter, session information may be stored for transmission and/or display, as described herein. Further, in accordance with implementations of the current subject matter, session information may be used to control operation of the vaporizer device and may be established or set by a user.

The vaporizer device and/or vaporizer system provided by the communication between the vaporizer device 100, the user device 305, and/or the remote server 307 (described with reference to FIG. 3) may include session control (also referred to as session metering). In some aspects, a user may find it desirable to monitor and/or control consumption of the vaporizable material. Such monitoring and/or control may beneficially allow a user to adjust an amount of vaporizable material available over a certain time period or session, a total time allowed for using the vaporizer, a time period between vaporizer sessions, other consumption settings to meet the needs of the user, and/or the like.

For example, in accordance with implementations of the current subject matter, session control may be provided by various preset session configurations established to control a session for the user. These preset session configurations may be displayed to the user on a user interface, allowing for the user to select a desired session. The preset session configurations may relate to session size, where session size refers to size of the dose of vaporizable material. In accordance with some implementations of the current subject matter, session size is determined based on the amount of energy used to produce vapor from the vaporizable material. The amount of energy is related to an amount of vapor produced. In some implementations, session size is based on an amount of energy applied to the heating element (e.g. how much heat is applied). In some implementations, session size is based on an amount of power applied to the heating element, a voltage applied to the heating element, a current applied to the heating element, a resistance applied to the heating element, or combinations thereof. In some implementations, session size is based on the energy applied to the heating element over a time period, the power applied to the heating element over a time period, the voltage applied to the heating element over a time period, the current applied to the heating element over a time period, the resistance applied to the heating element over a time period, or combinations thereof.

According to some aspects, available session sizes may include micro, small, medium, or large, signifying how much vapor is being produced for inhalation by a user. Other descriptive terms or identifiers (e.g., numeric values, symbols, and the like) may also be used for session sizes, and the implementations described herein are not limited to the specific terms describing the session size. For example, in some implementations, numeric values may correspond to session sizes expressed in units of mass, which may reflect precise estimates or estimates within a defined confidence interval.

Additionally, in accordance with implementations of the current subject matter, a temperature may be selected to be used for the vaporizer session. The temperature may be selected to adjust the strength of vapor being produced (for example, higher temperatures may produce a denser vapor (e.g., a greater mass of aerosol or greater total particulate matter) compared to vapor produced from a lower temperature). The selection of the temperature may in some implementations affect the session size. For example, a higher temperature may result in a shorter time to complete the selected session size.

The temperature may be based on a user selection via selection on the user interface generated by the vaporizer application. For example, the temperature of the vaporizer device may be adjusted by using a graphical user interface that allows both gross and precise control of the vaporizer temperature with, for example, a single finger. For example, a display of the temperature visually indicating the current temperature and/or target temperature of the vaporizer may be used to adjust the temperature up or down (within a range).

Alternatively, a preset temperature (which may be user, system, or cartridge defined and may be based on various factors such as for example user preferences, crowdsourced information, type of vaporizable material, and/or the like) may be applied for the vaporizer session. If a user does not specify a desired temperature, the preset temperature may be a default setting (e.g., a default provided by the vaporizer device or a default corresponding to the vaporizable material (e.g., a strain of cannabinoids)). In other examples, the user selection may override the preset temperature. In accordance with some implementations of the current subject matter, once a session starts, temperature is set and cannot be changed. In accordance with additional implementations, a temperature setting may carry over from a previous vaporizer session.

Preset temperature settings may be chosen based on desired outcomes. For example, one such setting may initiate a temperature boost when puffing and an auto cool down when not puffing; while another setting may gradually ramp up the temperature. Some preset temperature settings may aggressively affect temperature and thus vapor production more than other preset temperature settings. Another preset temperature setting may ramp down the temperature to a standby temperature.

Once the session size and/or temperature are selected, through for example user interaction on the vaporizer application, the vaporizer session according to the selected session size may begin. Alternatively, the vaporizer session may begin once other feedback or input is received, such as for example a user inhalation or puff or other defined action.

A visual indication of the status of the vaporizer session may be provided to the user via the vaporizer application. For example, a status or progress bar indicating a completed percentage of the vaporizer session may be displayed and continuously updated (i.e., progress is updated live while puffing). The status bar may be indicative of the amount of energy supplied to a heating element and may be a representation indicating amount of vaporizable material inhaled. Consistent with implementations of the current subject matter, the status bar may indicate a cumulative amount of energy supplied to the heating element; thus if a portion of the status bar is filled, this may indicate a percentage of the amount of energy supplied compared to a total amount of energy for the vaporizer session. When the total amount of energy for the vaporizer session is provided, the status bar may be filled, indicating that the vaporizer session is complete.

According to some aspects, once the vaporizer session is completed, the vaporizer may be locked for a preset amount of time (also referred to as a lockout period and a predefined lockout period), for example 30 seconds. Other time periods may be used for the locked amount, and such time periods may be user or system defined. During such a lockout period, user puffing does not produce any vapor. For example, during the lockout period the vaporizer device 100 does not allow activation of the heating element. During the lockout period, consistent with implementations of the current subject matter, if the user puffs or draws on the mouthpiece, vapor is not produced. Once the lockout period ends, the session size may be set as the same as the previous session unless otherwise updated by the user. There may be an option to override or end the lockout period. If such an option is selected, the vaporizer device 100 is provided with data or a signal indicative of the user selection to override the lockout period, and the vaporizer device 100 may then accordingly respond to the user puffing or drawing on the mouthpiece and/or to selection of a new vaporizer session. In some implementations, the lockout period may not be overridden by the user. In some implementations, the user or a manufacturer may establish settings regarding use of the lockout period. For example, the user or the manufacturer may establish a certain number of lockout periods that may be overridden in a certain time period.

In accordance with implementations of the current subject matter, incorporating session options with temperature control provides for an extra level of user control. Additionally, the session size and temperature selection options allow for a user to control and replicate experiences (e.g., by using settings from previous sessions).

In general, any of the vaporizer devices described herein may estimate, measure, and/or predict the amount of vapor and/or material (including active ingredients) in the vapor that may be delivered to a user. For example, the devices described herein may be used to determine and/or control dosing of the vaporizable material. For example, the current subject matter includes vaporizer devices and methods of using such vaporizer devices for accurate and controlled dose delivery of an active ingredient in a vaporizable material (e.g., nicotine, cannabis, and any other active ingredient/drug) based on user specified, medical, switching or cessation needs. Session configurations for a user may be controlled by another entity, for example, a health care provider, a manufacturer, and/or the like.

Information about the cartridge and/or a vaporizable material held in the cartridge may be particularly helpful in determining dose. For example information such as one or more of: the type of vaporizable material (e.g., nicotine, cannabis, etc.), the concentration of vaporizable material, the content of the vaporizable material, the amount of vaporizable material, the configuration of the cartridge (e.g., heater, electrical properties, etc.), the lot number of the cartridge, the date of manufacture of the cartridge, expiration date, the thermal properties of the vaporizable material, etc. may be used to accurately estimate dose. In some implementations of the current subject matter, dose and/or use information may be stored (written) on the cartridge (e.g., in a memory).

After completion of a vaporizer session, it may be desirable to control the start of a new session. In some aspects, the user may wish to limit or monitor the vaporizer session for a given time period (e.g., sessions per hour, day, week, month, etc.). In order to clearly distinguish vaporizer sessions from one another, the vaporizer device and/or the user device may require a specific user input, wait time between sessions, device setting or status, or other criteria before starting a new vaporizer session.

As previously described herein, a user may apply session control features, which limits the amount of energy supplied to the heater 166 to result in a controlled amount of vapor being produced from the vaporizable material. In accordance with some implementations of the current subject matter, available session sizes signify or are representative of how much vapor is being produced for inhalation by a user. A linear correlation exists between the amount of energy supplied and an amount of vaporizable material removed from the cartridge 150. The amount of the vaporizable material removed is referred to as total particulate matter (sometimes referred to as TPM).

Figures 5A, 5B:
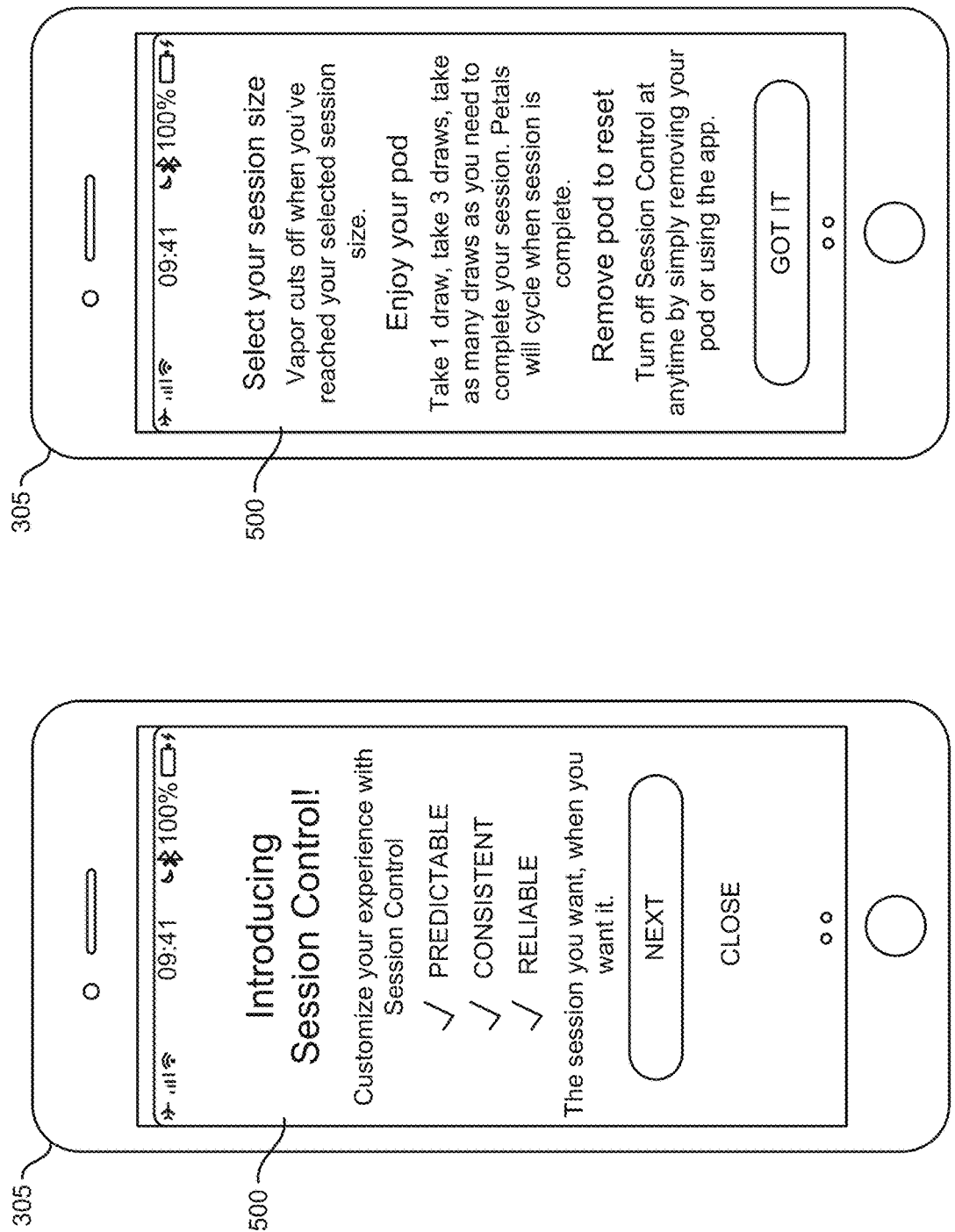

FIG. 5A-FIG. 5H illustrate an example user interface (UI) 500 for selecting a particular session in accordance with implementations of the current subject matter. The UI 500 may be generated and displayed on the user device 305. As shown in FIG. 5A and FIG. 5B, the UI 500 provides general information about utilizing preset session configurations for session control, as well as information related to the operation (e.g., select a desired size, remove the cartridge to reset session control, etc.).

Figures 5C, 5D:
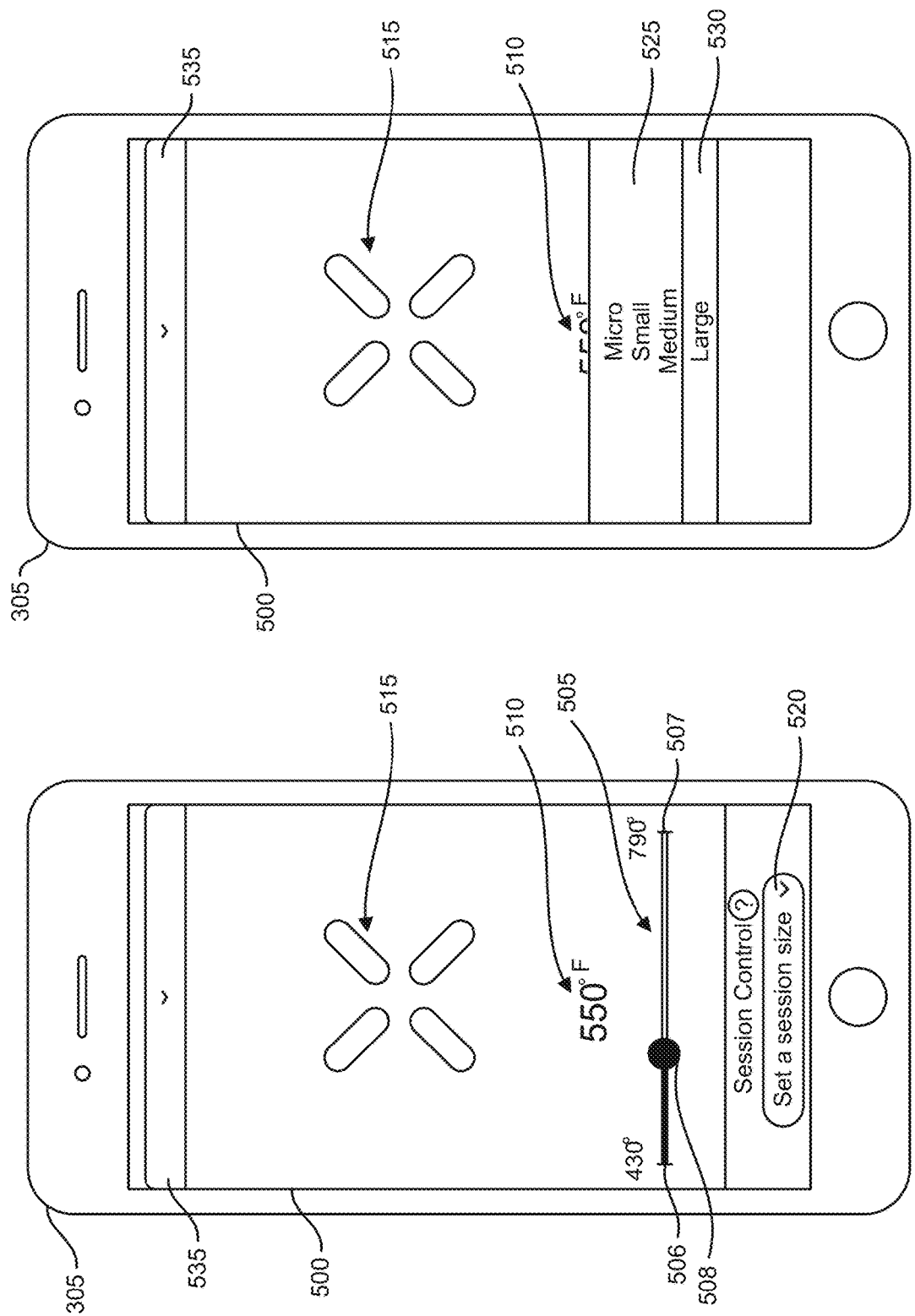

As shown in FIG. 5C, the UI 500 may include a slideable selection bar 505 that may be used to select a temperature for the vaporizer session. In some implementations the slideable selection bar 505 may include a low end 506 representing the lowest temperature that may be selected, and a high end 507 representing the highest temperature that may be selected. The low end 506 and/or the high end 507 may be predetermined and/or may be based on various factors, such as the vaporizable material, properties of the vaporizable material, user preferences, crowdsourced information, and the like. In some implementations, the low end 506 and/or the high end 507 are established values used for each session. In some implementations, the low end 506 and/or the high end 507 are set by a manufacturer of the vaporizer device 100 and/or the cartridge 150. The slideable selection bar 505 may further include a slideable icon 508 that is configured to be slid by user interaction on the UI 500 between the low end 506 and the high end 507 to select the temperature for the vaporizer session. Once the user positions the slideable icon 508 along the slideable selection bar 505, the temperature may be set at a temperature point at which the slideable icon 508 is positioned. The slideable icon 508 is shown as a circle but may be of various other shapes or forms (e.g., square, rectangle, oval, hash mark, star, etc.).

The UI 500 may further include one or more temperature icons representative of the temperature selection. For example, a first temperature icon 510 may be a numerical representation (in degrees Celsius or Fahrenheit) of the temperature point at which the slideable icon 508 is positioned. A second temperature icon 515 may be for example a symbol, figure, picture, or character element whose properties change based on the temperature selection. For example, a color of the second temperature icon 515 may be correlated with the selected temperature, where for example shades of blue represent a lower temperature and shades of red represent a higher temperature. Shading, highlighting, or other distinguishing markings may be used for the second temperature icon 515 to represent the temperature selection.

Figure 9:
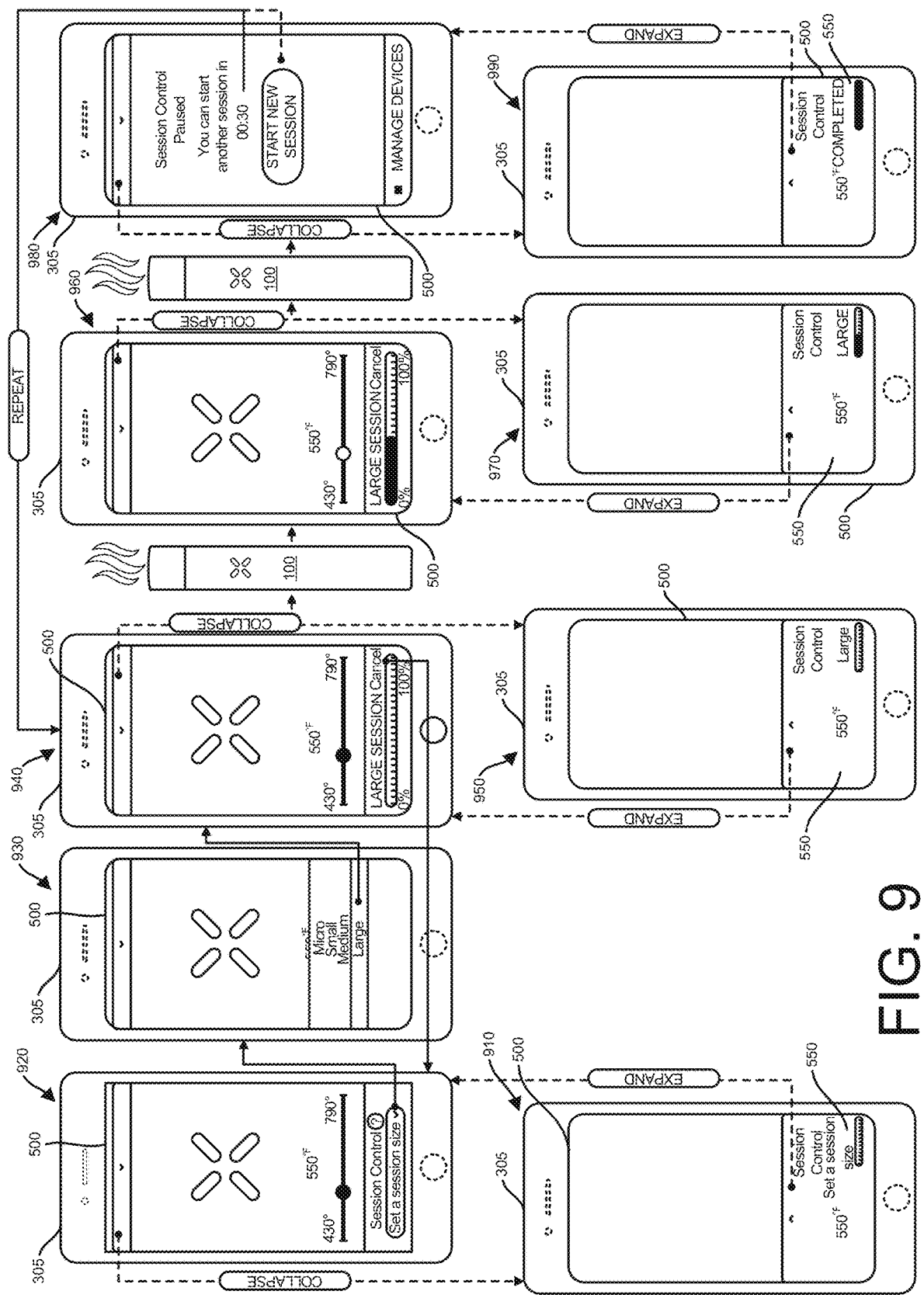
FIG. 9 shows a process flow chart illustrating operational features consistent with implementations of the current subject matter.

The UI 500 may further include a collapse selection feature 535, selection of which may result in the session control features being provided in a collapsed window 550 (shown in and described with respect to FIG. 9).

The UI 500 may also include, as shown in FIG. 5C, a dropdown menu 520, selection of which results in a session size selection display 525 (see FIG. 5D) of selectable session size options for the vaporizer session. User interaction on the UI 500 may result in the user selecting a particular session size from the session size selection display 525 (session size selection 530).

FIG. 5E provides an example representation of the UI 500 when the temperature and the session size are selected. As shown, the first temperature icon 510 and the second temperature icon 515 may indicate the selected temperature. A selected session size indicator 545 may be provided on the UI. The selected session size indicator 545 may express the selected session size in words or through one or more symbols or other representations. As further shown in FIG. 5E, the UI 500 also includes a status bar 540, which may be used to indicate progress through the vaporizer session. For example, the status bar 540 may indicate a fraction or percentage of the vaporizer session that has been completed and/or a fraction or percentage of the vaporizer session that remains. In one implementation, the status bar 540 is a horizontally elongated window that becomes filled during the vaporizer session to signify progression through the vaporizer session. The status bar 540 may be of various other forms, for example highlighted or distinguishable hash marks along a line, a circle that is filled in a clockwise direction, a vertically elongated window that is filled, and the like.

FIG. 5F provides an example representation of the UI 500 when the vaporizer session has started. As shown the status bar 540 is partially filled to illustrate the user's progress through the vaporizer session. One or more properties of the slideable icon 508 may change to indicate the vaporizer session is in progress and that the selected temperature cannot be adjusted (i.e., the temperature selection is locked and not adjustable). For example, the slideable icon 508 may be a circle that is filled in when the temperature is not yet set. When the vaporizer session is in progress, the slideable icon 508 may change to an empty circle. In some implementations, a characteristic of the slideable icon 508 may change to represent that the vaporizer session is in progress and/or that the temperature selection is set and cannot be adjusted. For example, the slideable icon 508 may change shape or color, may become highlighted momentarily or throughout the vaporizer session, may flash one or more times and/or at a predetermined frequency during the vaporizer session, or may have another distinguishing feature to signify that the vaporizer session is in progress and that the selected temperature cannot be adjusted.

Consistent with implementations of the current subject matter, when the vaporizer session is in progress, the session size selection may also be locked and is not adjustable.

FIG. 5G provides an example representation of the UI 500 at a point of further progression through the vaporizer session as compared to the representation in FIG. 5F. As shown, the status bar 540 is filled in further to represent the further progression of the vaporizer session.

FIG. 5H is an example representation of the UI 500 when the vaporizer session is completed. The UI 500 may include a lock screen 548 indicative of the vaporizer session being completed. The lock screen 548 may include information related to the lockout period (e.g., time remaining before another vaporizer session may be started). The lock screen 548 may also include a start new session button 549, the selection of which initiates a new vaporizer session during the lockout period. In some implementations, if the start new session button 549 is not selected during the lockout period, the user must wait until the lockout period has lapsed to start a new vaporizer session.

FIG. 6A-FIG. 6J illustrate features of exemplary user interfaces that may be presented by an application for selecting a temperature, in accordance with some implementations of the current subject matter.

FIG. 6A and FIG. 6B illustrate details of the UI 500 that allows for the user to select a desired temperature by moving or sliding through a range of temperatures. The UI 500 also includes, as previously described, other visual indicators to further illustrate the selected temperature (e.g., a single blue or lightly shaded indicator for a low temperature (FIG. 6A) and a plurality of red or dark shaded indicators for a high temperature (FIG. 6B)). As shown, the dropdown menu 520 is also provided for the user to indicate a desired session size.

Figure 6D:
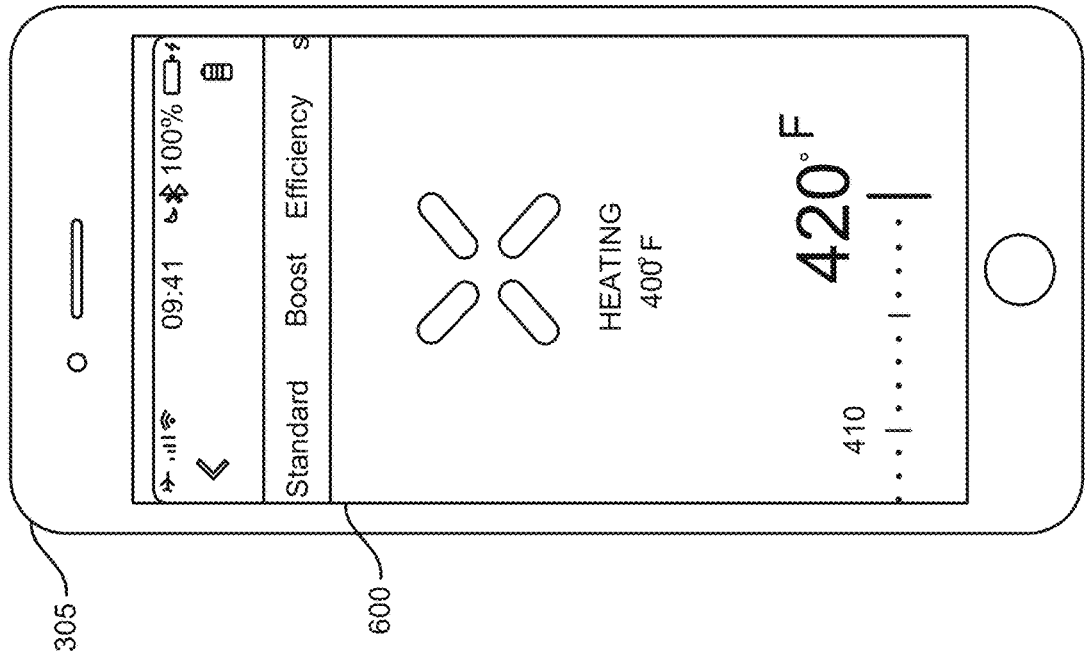
Figure 6C:
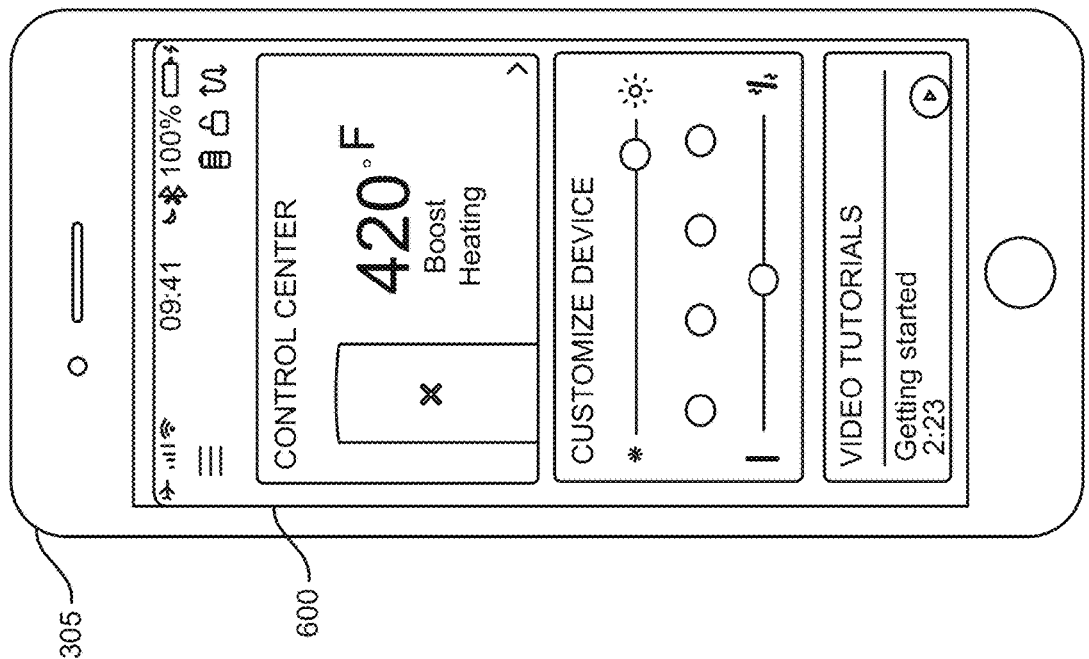
Figure 6F:
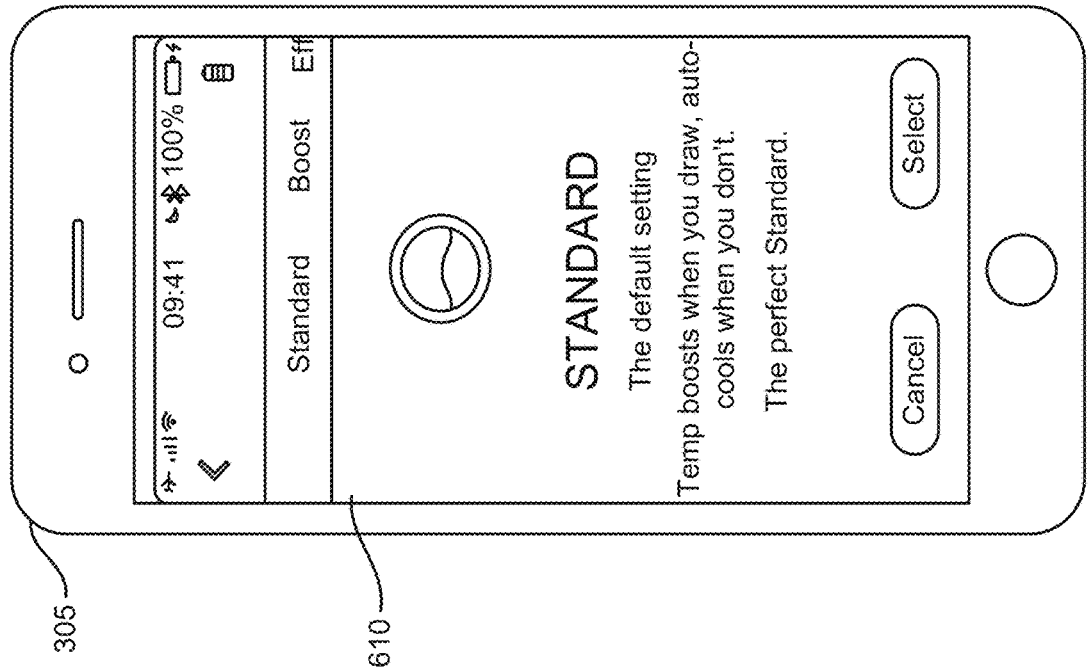
Figure 6E:
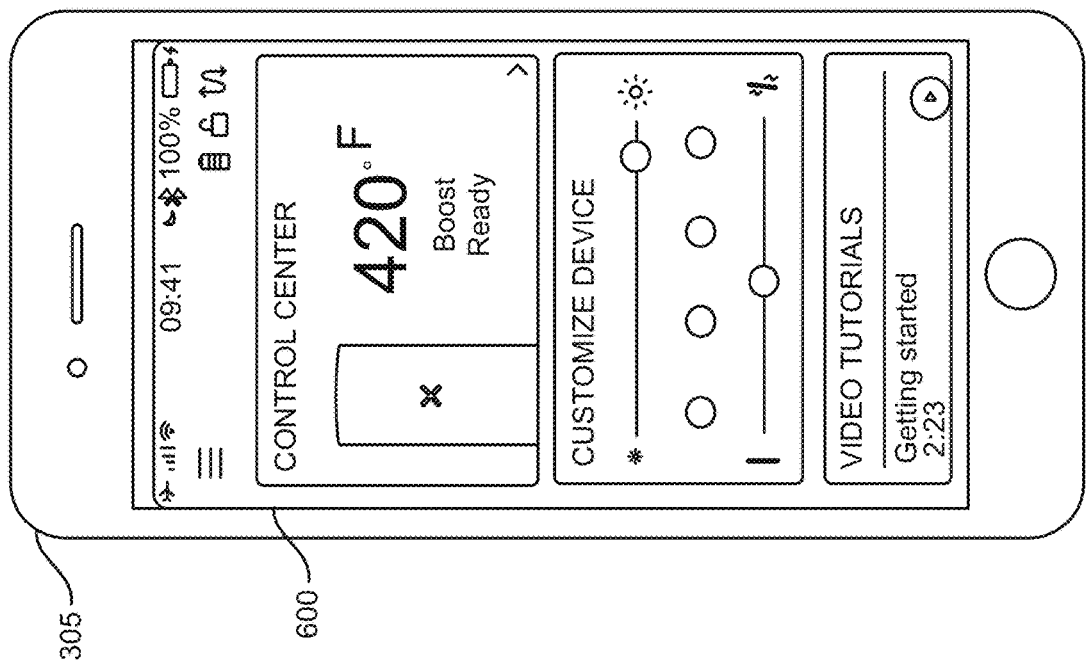
Figure 6H:
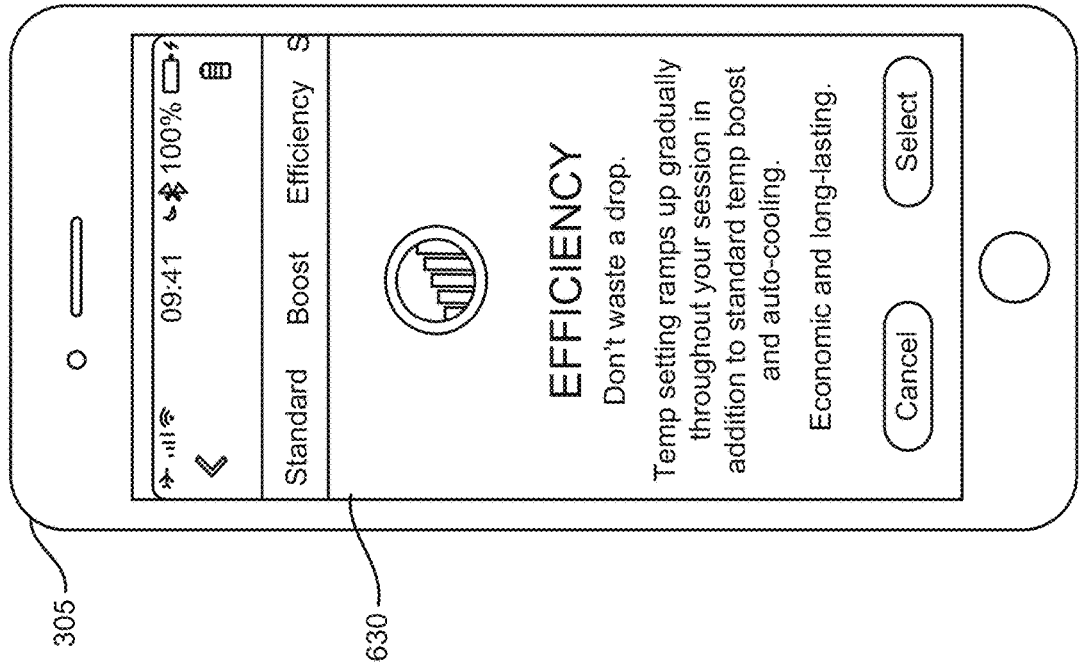
Figure 6G:
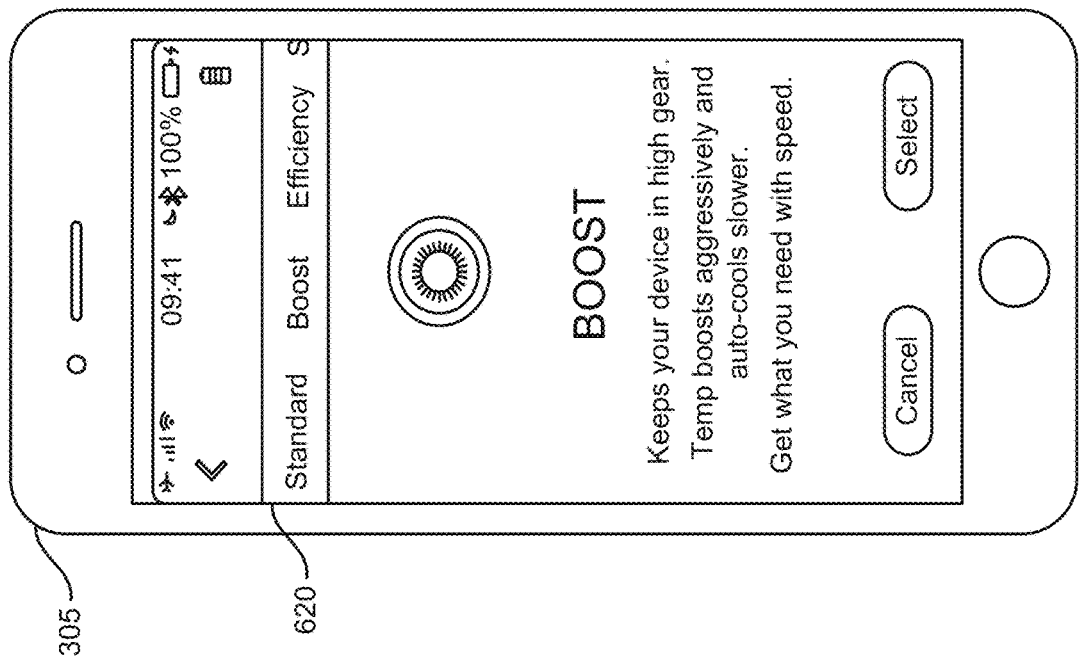

FIG. 6C-FIG. 6E illustrate example UIs that provide status and control information, which may be related to preset temperature settings. For example, UI 600 in FIG. 6C-FIG. 6E illustrates information related to a boost temperature setting. FIG. 6F-FIG. 6J illustrate example UIs 610, 620, 630, 640, and 650, respectively, that provide information on various preset temperature settings, including options to select a particular preset temperature setting.

As noted above, when a cartridge is removed from and re-inserted into the vaporizer body, the pre-selected or preconfigured parameters (e.g., those from a previous session) may be automatically applied. Alternatively, the device may reset to baseline parameters, which may be user or system defined and/or customizable and which may be overridden.

Figure 7:
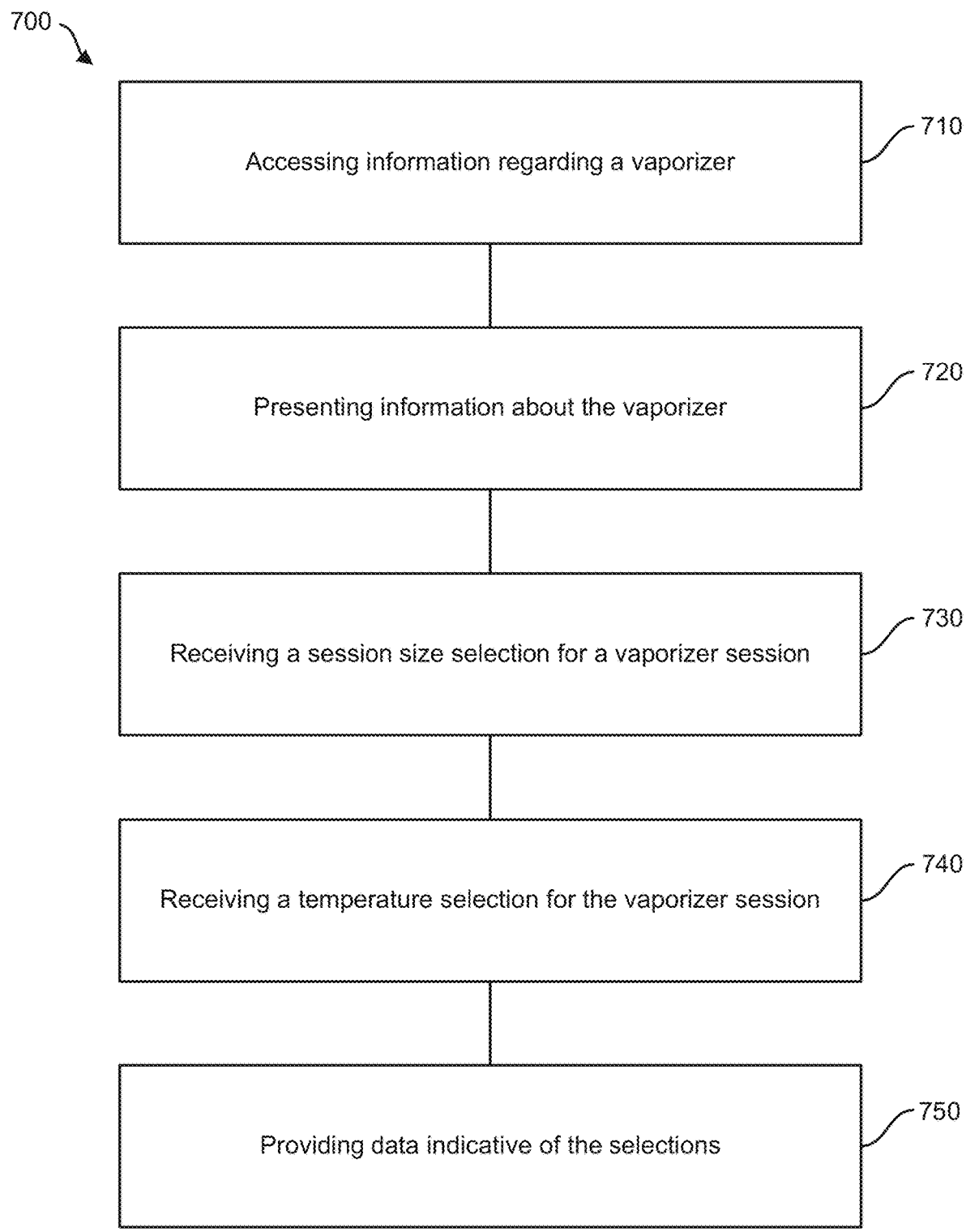
FIG. 7 shows a process flow chart illustrating features of a method consistent with some example implementations of the current subject matter.

With reference to FIG. 7, a process flow chart 700 illustrates features of a method, which may optionally include some or all of the following.

At 710, information regarding a vaporizer device 100 is accessed through operation of an application executing on one or more programmable processors. For example, when the session control application is being executed on the user device 305, the application may query the vaporizer device 100, through the wireless communication circuitry 142, to obtain information relating to the vaporizer device 100, such as the type of vaporizable material in the cartridge 150 and/or predefined settings (e.g., user settings and/or preferences, operational settings, etc.) stored in the memory 146.

At 720, information about the vaporizer device 100 is presented using a user interface generated on a display (e.g., of the user device 305) by the one or more processors. For example, one or more adjustable or preset parameters for a vaporizer session of the vaporizer device 100 may be displayed on the UI. The parameters may include temperature and session size. As previously described, the temperature may be preset based on a number of factors or may be adjustable or selectable. Similarly, the session size may be preset or adjustable or selectable.

At 730, a session size selection for the vaporizer session may be received by the user device 305. The session size selection may be provided by user input and/or user interaction with the UI consistent with implementations of the current subject matter as described herein.

At 740, a temperature selection indicating a temperature for the vaporizer session may be received by the user device 305. The temperature selection may be provided by user input and/or user interaction with the UI consistent with implementations of the current subject matter as described herein.

At 750, data indicative of the selections (e.g., the session size selection and the temperature selection) may be provided by the user device 305 to the controller 128 of the vaporizer device 100. The data indicative of the selection may include operational settings to cause the vaporizer device 100 to operate consistent with the selections. For example, a particular session size may be correlated with a certain amount of energy to be provided to the heating element. Thus the controller 128 may output the certain amount of energy and may cause the heater circuitry 130 to reach the selected temperature.

Figure 8:
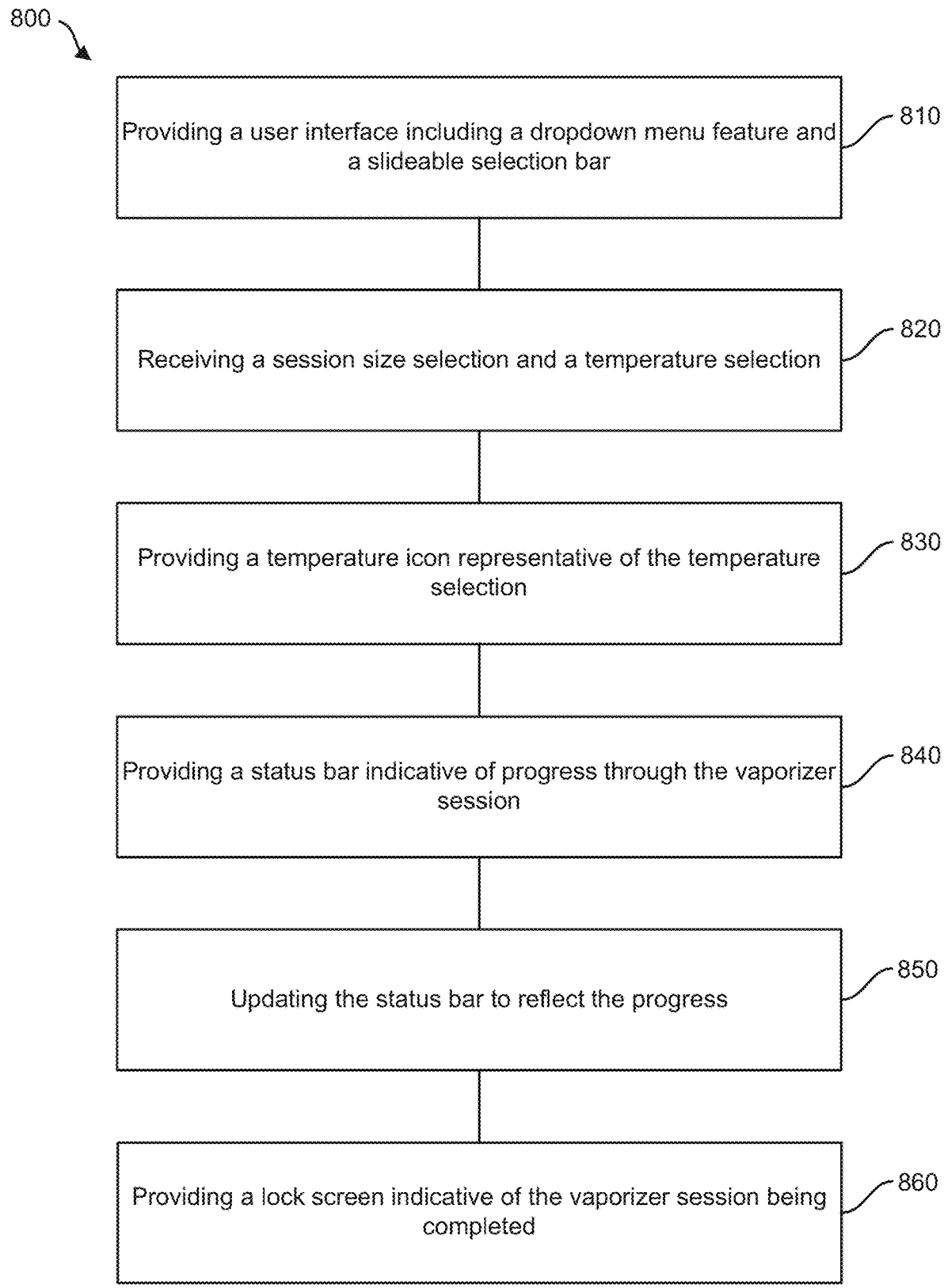
FIG. 8 shows a process flow chart illustrating features of another method consistent with some example implementations of the current subject matter.

With reference to FIG. 8, a process flow chart 800 illustrates features of a method, which may optionally include some or all of the following.

At 810, the user interface 500 including the dropdown menu 520 and the slideable selection bar 505 is provided on, for example, the user device 305 by executing the session control application. The dropdown menu 520 may include a plurality of selectable session size options for a vaporizer session of the vaporizer device 100. For example, selection of the dropdown menu 520 may result in the session size selection display 525 (see FIG. 5D) of selectable session size options for the vaporizer session. User interaction on the UI 500 may result in the user selecting a particular session size from the session size selection display 525 (session size selection 530). The slideable selection bar 505 includes the slideable icon 508, movable between the low end 506 and the high end 507 to select a temperature between the low end 506 and the high end 507 for the vaporizer session of the vaporizer device 100.

At 820, the session size selection and the temperature selection are received by the user device 305. For example, through user interaction with the dropdown menu 520 the session size may be selected, and through user interaction with the slideable icon 508 on the slideable selection bar 505 the temperature may be selected.

At 830, one or more of the first temperature icon 510 and the second temperature icon 515 may be provided on the UI 500 to represent the temperature selection for the vaporizer session. For example, with reference to FIG. 5E, the first temperature icon 510 may be a numerical representation (in degrees Celsius or Fahrenheit) of the temperature point at which the slideable icon 508 is positioned. The second temperature icon 515 may be for example a symbol, figure, picture, or character element whose properties change based on the temperature selection. For example, a color of the second temperature icon 515 may be correlated with the selected temperature, where for example shades of blue represent a lower temperature and shades of red represent a higher temperature.

At 840, the status bar 540 indicative of progress through the vaporizer session may be provided on the UI 500. For example, the status bar 540 may indicate a fraction or percentage of the vaporizer session that has been completed and/or a fraction or percentage of the vaporizer session that remains. In one implementation, the status bar 540 is a horizontally elongated window that becomes filled during the vaporizer session to signify progression through the vaporizer session. As described herein, the status bar 540 may represent a fraction of the cumulative amount of energy at a given time during the vaporizer session over the total amount of energy for the vaporizer session (where the total amount of energy for the vaporizer session is based on the selected session size).

At 850, the status bar 540 is updated to reflect the progress through the vaporizer session. For example, with reference to FIG. 5F which provides an example representation of the UI 500 when the vaporizer session has started, the status bar 540 is partially filled to illustrate the user's progress through the vaporizer session.

At 860, the lock screen 548 is provided on the UI 500. The lock screen 548 may be indicative of the vaporizer session being completed. In some implementations, the lock screen 548 may indicate if the vaporizer session is temporarily paused. With reference to FIG. 5H, which provides an example representation of the UI 500 when the vaporizer session is completed, the lock screen 548 may include information related to the lockout period (e.g., time remaining before another vaporizer session may be started). The lock screen 548 may also include the start new session button 549, the selection of which initiates a new vaporizer session during the lockout period.

FIG. 9 shows a process flow chart illustrating operational features of the vaporizer session application consistent with implementations of the current subject matter.

Representation 910 represents a default collapsed state of the UI 500. As described herein, selection of the collapse selection feature 535 of the UI 500 may result in the session control features being provided in the collapsed window 550 as shown in 910 of FIG. 9. In the default collapsed state, the collapsed window 550 provides an indication that the session size has not yet been selected. The collapsed window 550 allows for the user to be able to view other information in the UI 500 while still having access to the session control features.

The user may expand the collapsed window 550 to be presented with the UI 500 (default state, representation 920) in which the session size and the temperature need to be selected to initiate the session control features consistent with implementations of the current subject matter. In the default state, the user may use the slideable selection bar 505 with the slideable icon 508 to select a temperature between the low end 506 and the high end 507 for the vaporizer session of the vaporizer device 100. The user may go between the collapsed and expanded states as indicated.

Representation 930 indicates the UI 500 in a select size state in which the dropdown menu 520 is selected to indicate, in the session size selection display 525, the plurality of selectable session size options for the vaporizer session of the vaporizer device 100.

Representation 940 represents the UI 500 in a session set state in which the session size and the temperature for the vaporizer session have been selected. As shown by the status bar 540, the vaporizer session has not yet started. The representation 940 may be collapsed (e.g., via selection of the collapse selection feature 535) to representation 950, which represents a session set collapsed state. As shown in the representation 950 in the collapsed window 550, the vaporizer session is set (i.e., the temperature and the session size have been selected) but the vaporizer session has not yet started. The user may go between the collapsed and expanded states as indicated.

Once the user draws or inhales on the vaporizer device 100, the vaporizer session begins. Representation 960 represents the UI 500 in a session progress state. In the session progress state, the status bar 540 represents progress through the vaporizer session. Additionally, the slideable icon 508 may be changed (e.g., from a filled circle to an empty circle) to indicate the vaporizer session is in progress and that the selected temperature cannot be adjusted.

The representation 960 may be collapsed (e.g., via selection of the collapse selection feature 535) to representation 970, which represents a session progress collapsed state. As shown in the representation 970, details of the vaporizer session are shown in the collapsed window 550, including for example progress of the vaporizer session through the status bar 540 and the selected temperature.

As the user continues to draw on the vaporizer device 100, the user is able to access, via the UI 500, details related to the vaporizer session in either the session progress state (representation 960) or the session progress collapsed state (representation 970). The user may go between the collapsed and expanded states as indicated.

Representation 980 represents the UI 500 in a session completed state in which the vaporizer session is completed and the lock screen 548 is provided on the UI 500. The representation 980 may be collapsed to representation 990, which represents a session completed collapsed state, also indicating completion of the vaporizer session in the collapsed window 550. As shown in the representation 980, the user may select a new session via selection of the start new session button 549, in which case the representation 940 is provided.

The user may move between the expanded views of the UI 500 and the collapsed views of the UI including the collapsed window 550 during use of the session control application and during the vaporizer session as shown in FIG. 9. The collapsed views allow for the user to be kept apprised of the status of the vaporizer session while still being able to view on the UI 500 additional details. The expanded views allow for the user to be provided with a more detailed view of the vaporizer session and settings, as well as provide for more user control (e.g., selection of the temperature, selection of the session size, selection of the start new session button 549).

Figure 10:
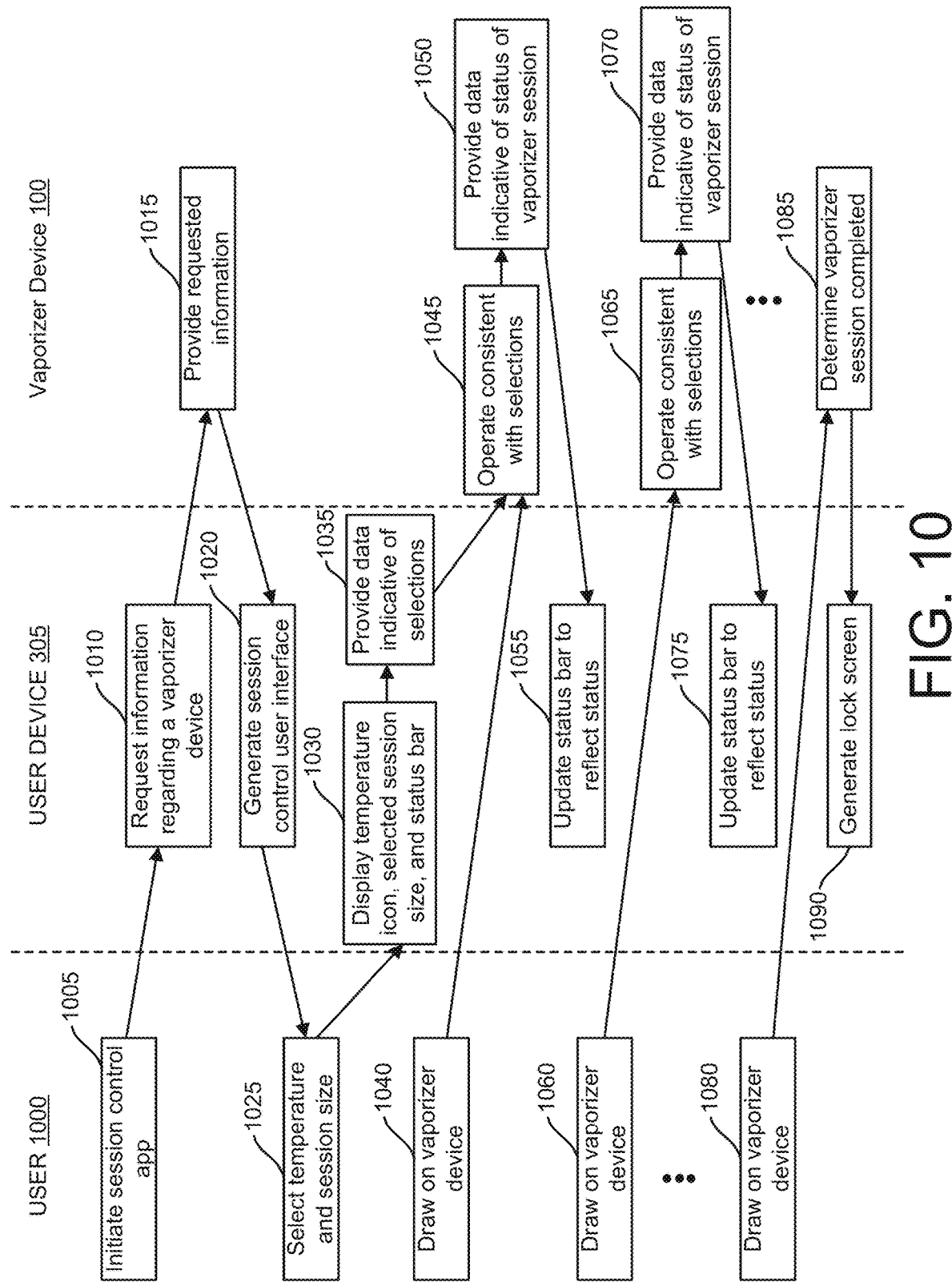
FIG. 10 shows a swim lane diagram illustrating operations of a user, a user device, and a vaporizer device consistent with implementations of the current subject matter.

FIG. 10 shows a swim lane diagram illustrating session control operations of a user 1000, the user device 305, and the vaporizer device 100 consistent with implementations of the current subject matter.

At 1005, the user 1000 may initiate the session control application through the user's user device 305. When the session control application is initiated the user device 305 may, at 1010, request information regarding the vaporizer device 100 from the vaporizer device 100. For example, the user device 305 may query the vaporizer device 100, through the wireless communication circuitry 142 of the vaporizer device 100, to obtain information relating to the vaporizer device 100, such as the type of vaporizable material in the cartridge 150 and/or predefined settings (e.g., predefined user settings and/or preferences, predefined operational settings, etc.) stored in the memory 146 of the vaporizer device 100 and/or associated with the cartridge 150 (e.g., accessible via communication with the remote server 307). In some implementations, the predefined settings may include predefined session size and/or predefined temperature.

At 1015, the vaporizer device 100 provides the requested information to the user device 305. In some implementations, operations 1010 and 1015 may be bypassed. For example, in some instances, the user device 305 may not need to query the vaporizer device 100 for predefined settings as such settings may not be relevant to use or may alternatively be stored in or otherwise accessible to the user device 305.

At 1020, the user device 305 generates the session control UI 500, for example as shown in FIGS. 5A, 5B, and/or 5C.

At 1025, the user 1000 selects the temperature and the session size. For example, through user interaction with the dropdown menu 520 the session size may be selected, and through user interaction with the slideable icon 508 on the slideable selection bar 505 the temperature may be selected. In instances in which one or more of the temperature and the session size are predefined (e.g., a predefined temperature based on the type of vaporizable material), the user 1000 may not need to or have access to set the temperature and/or the session size, but such predefined settings may be displayed to the user 1000.

At 1030, upon selection of the temperature and the session size, the user device 305 may generate on the UI 500 the first temperature icon 510, the second temperature icon 515, the selected session size indicator 545, and/or the status bar 540. Moreover, upon selection of the temperature and the session size, at 1035, the user device 305 may provide data indicative of the user selections to the vaporizer device 100. For example, the user device 305 may provide to the vaporizer device 100 operational data indicative of the selected session size and the selected temperature for the vaporizer session.

At 1040, the user 1000 may draw on a mouthpiece of the vaporizer device 100. The draw on the mouthpiece of the vaporizer device 100 together with the received operational data from the user device 305, may result in, at 1045, the vaporizer device 100 operating consistent with the user selections. The user drawing on the mouthpiece of the vaporizer device 100 may be detected by the vaporizer device 100. The operational data indicative of the user selections may include operational settings to cause the vaporizer device 100 to operate consistent with the selections. For example, a particular session size may be correlated with a certain total amount of energy to be provided to the heating element during the vaporizer session. Thus the controller 128 may output the total amount of energy to the heating element during the vaporizer session, and may cause the heater circuitry 130 to control the heating element to operate at the selected temperature.

At 1050, the vaporizer device 100 may provide, to the user device 305, status data indicative of the status of the vaporizer session. For example, the status data may include a cumulative amount of energy provided to the heating element. In some implementations, the vaporizer device 100 may provide the status data in response to a detection, by the vaporizer device 100, of the user drawing on the mouthpiece of the vaporizer device 100. At 1055, the user device 305 may use the status data indicative of the status of the vaporizer session to update the status bar 540 to reflect user progress of the vaporizer session.

As the user 1000 continues to draw on the mouthpiece of the vaporizer device 100, at 1060, the operational sequence of the vaporizer device 100 operating (at 1065) consistent with the user selections, the vaporizer device 100 providing (at 1070) status data indicative of the status of the vaporizer session to the user device 305, and the user device 305 (at 1075) updating the status bar 540 to reflect user progress of the vaporizer session may repeat. This operation sequence may repeat until, following the user 1000 drawing on the mouthpiece of the vaporizer device 100 at 1080, the vaporizer device 100 determines (at 1085) that the vaporizer session is completed. This determination may be based on, via a comparison operation by the vaporizer device 100, the cumulative amount of energy being equal to the total amount of energy for the selected vaporizer session. Following the determination at 1085 by the vaporizer device, the user device 305 may generate (based on data or signaling indicative of the vaporizer session being completed sent to the user device 305 from the vaporizer device 100) the lock screen 548 on the UI 500 to indicate to the user 1000 that the vaporizer session is completed and that the vaporizer device 100 is in the predefined lockout period.

During the predefined lockout period, user puffing does not produce any vapor. For example, during the lockout period the vaporizer device 100 does not allow activation of the heating element. During the lockout period, consistent with implementations of the current subject matter, if the user puffs or draws on the mouthpiece, vapor is not produced. Once the lockout period ends, the session size may be set as the same as the previous session unless otherwise updated by the user. There may be an option to override or end the lockout period. If such an option is selected, the vaporizer device 100 may be provided with, from the user device 305, data or a signal indicative of the user selection to override the lockout period, and the vaporizer device 100 may then accordingly respond to the user puffing or drawing on the mouthpiece (e.g., by activation of the heating element) and/or to selection of a new vaporizer session.

As described herein, consistent with some implementations of the current subject matter, session size is based on the amount of energy applied to the heating element. In some implementations, session size is based on an amount of power applied to the heating element, a voltage applied to the heating element, a current applied to the heating element, a resistance applied to the heating element, or combinations thereof. In some implementations, session size is based on the energy applied to the heating element over a time period, the power applied to the heating element over a time period, the voltage applied to the heating element over a time period, the current applied to the heating element over a time period, the resistance applied to the heating element over a time period, or combinations thereof.

In some examples, the vaporizable material may include a viscous liquid such as, for example a cannabis oil. In some variations, the cannabis oil comprises between 0.3% and 100% cannabis oil extract. The viscous oil may include a carrier for improving vapor formation, such as, for example, propylene glycol, glycerol, medium chain triglycerides (MCT) including lauric acid, capric acid, caprylic acid, caproic acid, etc., at between 0.01% and 25% (e.g., between 0.1% and 22%, between 1% and 20%, between 1% and 15%, and/or the like). In some variations the vapor-forming carrier is 1,3-Propanediol. A cannabis oil may include a cannabinoid or cannabinoids (natural and/or synthetic), and/or a terpene or terpenes derived from organic materials such as for example fruits and flowers. For example, any of the vaporizable materials described herein may include one or more (e.g., a mixture of) cannabinoid including one or more of: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), Tetrahydrocannabinol, Cannabidiol (CBD), Cannabinol (CBN), Tetrahydrocannabinolic Acid (THCA), Cannabidioloc Acid (CBDA), Tetrahydrocannabivarinic Acid (THCVA), one or more Endocannabinoids (e.g., anandamide, 2-Arachidonoylglycerol, 2-Arachidonyl glyceryl ether, N-Arachidonoyl dopamine, Virodhamine, Lysophosphatidylinositol), and/or a synthetic cannabinoids such as, for example, one or more of: JWH-018, JWH-073, CP-55940, Dimethylheptylpyran, HU-210, HU-331, SR144528, WIN 55,212-2, JWH-133, Levonantradol (Nantrodolum), and AM-2201. The oil vaporization material may include one or more terpene, such as, for example, Hemiterpenes, Monoterpenes (e.g., geraniol, terpineol, limonene, myrcene, linalool, pinene, Iridoids), Sesquiterpenes (e.g., humulene, farnesenes, farnesol), Diterpenes (e.g., cafestol, kahweol, cembrene and taxadiene), Sesterterpenes, (e.g., geranylfarnesol), Triterpenes (e.g., squalene), Sesquarterpenes (e.g, ferrugicadiol and tetraprenylcurcumene), Tetraterpenes (lycopene, gamma-carotene, alpha- and beta-carotenes), Polyterpenes, and Norisoprenoids. For example, an oil vaporization material as described herein may include between 0.3-100% cannabinoids (e.g., 0.5-98%, 10-95%, 20-92%, 30-90%, 40-80%, 50-75%, 60-80%, etc.), 0-40% terpenes (e.g., 1-30%, 10-30%, 10-20%, etc.), and 0-25% carrier (e.g., medium chain triglycerides (MCT)).

In any of the oil vaporizable materials described herein (including in particular, the cannabinoid-based vaporizable materials), the viscosity may be within a predetermined range. The range may be between, at room temperature (23° C.) about 30 cP (centipoise) and 115 kcP (kilocentipoise), between 30 cP and 200 kcP, although higher viscosities and/or lower viscosities may be implemented as well. For example, the viscosity may be between 40 cP and 113 kcP at room temperature. Outside of this range, the vaporizable material may fail in some instances to wick appropriately to form a vapor as described herein. In particular, it is typically desired that the oil may be made sufficiently thin to both permit wicking at a rate that is useful with the apparatuses described herein, while also limiting leaking (e.g., viscosities below that of ~30 cP at room temperature might result in problems with leaking).

Although the disclosure, including the figures, described herein may described and/or exemplify these different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" "or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method, comprising:
providing a user interface comprising a dropdown menu and a slideable selection bar, the dropdown menu comprising a plurality of selectable session size options for a vaporizer session of a vaporizer device, and the slideable selection bar comprising a slideable icon configured to select a temperature for the vaporizer session of the vaporizer device;
receiving, from the user interface, a session size selection and a temperature selection;
providing, on the user interface, a temperature icon representative of the temperature selection;
providing, on the user interface, a status bar indicative of progress through the vaporizer session, wherein the vaporizer session is based on the session size selection and the temperature selection;
updating, on the user interface, the status bar to reflect the progress through the vaporizer session; and
locking, in response to a determination that the vaporizer session is in progress, the session size selection and the temperature selection such that the session size selection and the temperature selection are not adjustable via the user interface while the vaporizer session is in progress.

2. The method of claim 1, wherein each of the plurality of selectable session size options corresponds to a predetermined amount of energy to apply to a heating element of the vaporizer device.

3. The method of claim 1, wherein the slideable icon is configured to be moved along the slideable selection bar between a predefined low end temperature and a predefined high end temperature.

4. The method of claim 1, further comprising:
changing, on the user interface and in response to the determination that the vaporizer session is in progress, a characteristic of the slideable icon.

5. The method of claim 1, wherein providing the temperature icon representative of the temperature selection comprises one or more of providing a first temperature icon comprising a numerical representation of the temperature selection and providing a second temperature icon comprising a symbol shaded in correlation with the temperature selection.

6. The method of claim 1, wherein the status bar comprises a horizontally elongated window, wherein the horizontally elongated window is filled during the vaporizer session indicative of the progress through the vaporizer session.

7. The method of claim 6, wherein the progress through the vaporizer session comprises a cumulative amount of energy provided to a heating element of the vaporizer device over a total amount of energy to be provided to the heating element, wherein the total amount of energy to be provided is based on the session size selection.

8. The method of claim 7, wherein updating the status bar to reflect the progress through the vaporizer session comprises filling the horizontally elongated window to represent a fraction comprising the cumulative amount of energy over the total amount of energy.

9. The method of claim 1, further comprising:
providing, on the user interface and in response to selection of a collapse selection feature, a collapsed window, the collapsed window providing a representation of the temperature selection, the session size selection, and the status bar.

10. The method of claim 9, further comprising:
expanding, on the user interface and in response to selection of the collapsed window, the collapsed window.

11. The method of claim 1, further comprising:
providing, on the user interface, a lock screen indicative of the vaporizer session being completed;
wherein the lock screen comprises a start new session button, wherein selection of the start new session initiates a new vaporizer session during a lockout period.

12. The method of claim 11, wherein the lockout period is predefined and/or non-adjustable.

13. An apparatus, comprising:
at least one data processor; and
at least one memory storing instructions which, when executed by the at least one data processor, cause operations comprising:
providing a user interface on the apparatus, the user interface comprising a dropdown menu and a slideable selection bar, the dropdown menu comprising a plurality of selectable session size options for a vaporizer session of a vaporizer device, and the slideable selection bar comprising a slideable icon configured to select a temperature for the vaporizer session of the vaporizer device, wherein the apparatus and the vaporizer device are in communication with one another;
receiving, from the user interface, a session size selection and a temperature selection;
providing, on the user interface, a temperature icon representative of the temperature selection;
providing, on the user interface, a status bar indicative of progress through the vaporizer session, wherein the vaporizer session is based on the session size selection and the temperature selection;
updating, on the user interface, the status bar to reflect the progress through the vaporizer session; and
locking, in response to a determination that the vaporizer session is in progress, the session size selection and the temperature selection such that the session size selection and the temperature selection are not adjustable via the user interface while the vaporizer session is in progress.

14. The apparatus of claim 13, wherein each of the plurality of selectable session size options corresponds to a predetermined amount of energy to apply to a heating element of the vaporizer device.

15. The apparatus of claim 13, wherein the slideable icon is configured to be moved along the slideable selection bar between a predefined low end temperature and a predefined high end temperature.

16. The apparatus of claim 13, wherein the instructions, when executed, cause operations further comprising:
changing, on the user interface and in response to the determination that the vaporizer session is in progress, a characteristic of the slideable icon.

17. The apparatus of claim 13, wherein providing the temperature icon representative of the temperature selection comprises one or more of providing a first temperature icon comprising a numerical representation of the temperature selection and providing a second temperature icon comprising a symbol shaded in correlation with the temperature selection.

18. The apparatus of claim 13, wherein the status bar comprises a horizontally elongated window, wherein the horizontally elongated window is filled during the vaporizer session indicative of the progress through the vaporizer session.

19. The apparatus of claim 18, wherein the progress through the vaporizer session comprises a cumulative amount of energy provided to a heating element of the vaporizer device over a total amount of energy to be provided to the heating element, wherein the total amount of energy to be provided is based on the session size selection.

20. The apparatus of claim 19, wherein updating the status bar to reflect the progress through the vaporizer session comprises filling the horizontally elongated window to represent a fraction comprising the cumulative amount of energy over the total amount of energy.

21. The apparatus of claim 13, wherein the instructions, when executed, cause operations further comprising:
providing, on the user interface and in response to selection of a collapse selection feature, a collapsed window, the collapsed window providing a representation of the temperature selection, the session size selection, and the status bar.

22. The apparatus of claim 21, wherein the instructions, when executed, cause operations further comprising:
expanding, on the user interface and in response to selection of the collapsed window, the collapsed window.

23. The apparatus of claim 13, wherein the instructions, when executed, cause operations further comprising:
providing, on the user interface, a lock screen indicative of the vaporizer session being completed;
wherein the lock screen comprises a start new session button, wherein selection of the start new session initiates a new vaporizer session during a lockout period.

24. The apparatus of claim 23, wherein the lockout period is predefined and/or non-adjustable.

25. A non-transitory computer readable medium comprising a memory storing instructions, wherein the instructions, when executed by at least one data processor, are configured to cause the at least one data processor to execute a method comprising:
providing a user interface comprising a dropdown menu and a slideable selection bar, the dropdown menu comprising a plurality of selectable session size options for a vaporizer session of a vaporizer device, and the slideable selection bar comprising a slideable icon configured to select a temperature for the vaporizer session of the vaporizer device;
receiving, from the user interface, a session size selection and a temperature selection;
providing, on the user interface, a temperature icon representative of the temperature selection;
providing, on the user interface, a status bar indicative of progress through the vaporizer session, wherein the vaporizer session is based on the session size selection and the temperature selection;
updating, on the user interface, the status bar to reflect the progress through the vaporizer session; and
locking, in response to a determination that the vaporizer session is in progress, the session size selection and the temperature selection such that the session size selection and the temperature selection are not adjustable via the user interface while the vaporizer session is in progress.

26. A method comprising:
receiving, by a vaporizer device in communication with a user device, operational data indicative of a selected session size and a selected temperature for a vaporizer session, wherein the vaporizer device comprises a controller, wireless communication circuitry, heater control circuitry, and a heating element;
causing the vaporizer device to operate consistent with the operational data indicative of the selected session size and the selected temperature; and
providing, by the vaporizer device and to the user device, status data indicative of a status of the vaporizer session;
wherein the selected session size selection and the selected temperature are locked when the vaporizer session is in progress such that the selected session size and the selected temperature are not adjustable while the vaporizer session is in progress.

27. The method of claim 26, wherein the operational data indicative of the selected session size comprises a total amount of energy to be provided to the heating element during the vaporizer session.

28. The method of claim 27, wherein causing the vaporizer device to operate comprises providing the total amount of energy to the heating element during the vaporizer session.

29. The method of claim 27, wherein the status data indicative of the status of the vaporizer session comprises a cumulative amount of energy provided to the heating element.

30. The method of claim 27, further comprising:
determining, based on a comparison of a cumulative amount of energy provided to the heating element and the total amount of energy to be provided to the heating element, that the vaporizer session is completed; and
preventing, in response to the determination, activation of the heating element during a predefined lockout period.

31. The method of claim 30, further comprising:
providing, to the user device and in response to the determination, data indicative of the vaporizer session being completed.

32. The method of claim 30, further comprising:
receiving, from the user device, data indicative of the predefined lockout period being overridden; and
allowing, in response to the receipt of the data indicative of the predefined lockout period being overridden, activation of the heating element.

33. The method of claim 26, wherein causing the vaporizer device to operate comprises controlling, by the heater control circuitry, the heating element to operate at the selected temperature.

34. The method of claim 26, wherein causing the vaporizer device to operate is in response to a detection of a user drawing on a mouthpiece the vaporizer device.

35. The method of claim 26, wherein providing the status data is in response to a detection of a user drawing on a mouthpiece the vaporizer device.

36. The method of claim 26, further comprising:
providing, to the user device, information regarding the vaporizer device, wherein the information comprises a type of vaporizable material contained in the vaporizer device, predefined user settings, and/or predefined operational settings.

37. An apparatus, comprising:
at least one data processor; and
at least one memory storing instructions which, when executed by the at least one data processor, cause operations comprising:
receiving, from a user device in communication with the apparatus, operational data indicative of a selected session size and a selected temperature for a vaporizer session, wherein the apparatus comprises a controller, wireless communication circuitry, heater control circuitry, and a heating element;
causing the apparatus to operate consistent with the operational data indicative of the selected session size and the selected temperature; and
providing, to the user device, status data indicative of a status of the vaporizer session;
wherein the selected session size selection and the selected temperature are locked when the vaporizer session is in progress such that the selected session size and the selected temperature are not adjustable while the vaporizer session is in progress.

38. The apparatus of claim 37, wherein the operational data indicative of the selected session size comprises a total amount of energy to be provided to the heating element during the vaporizer session.

39. The apparatus of claim 38, wherein causing the apparatus to operate comprises providing the total amount of energy to the heating element during the vaporizer session.

40. The apparatus of claim 38, wherein the status data indicative of the status of the vaporizer session comprises a cumulative amount of energy provided to the heating element.

41. The apparatus of claim 38, wherein the instructions, when executed, cause operations further comprising:
determining, based on a comparison of a cumulative amount of energy provided to the heating element and the total amount of energy to be provided to the heating element, that the vaporizer session is completed; and
preventing, in response to the determination, activation of the heating element during a predefined lockout period.

42. The apparatus of claim 41, wherein the instructions, when executed, cause operations further comprising:
providing, to the user device and in response to the determination, data indicative of the vaporizer session being completed.

43. The apparatus of claim 41, wherein the instructions, when executed, cause operations further comprising:
receiving, from the user device, data indicative of the predefined lockout period being overridden; and
allowing, in response to the receipt of the data indicative of the predefined lockout period being overridden, activation of the heating element.

44. The apparatus of claim 37, wherein causing the apparatus to operate comprises controlling, by the heater control circuitry, the heating element to operate at the selected temperature.

45. The apparatus of claim 37, wherein causing the apparatus to operate is in response to a detection of a user drawing on a mouthpiece of the apparatus.

46. The apparatus of claim 37, wherein providing the status data is in response to a detection of a user drawing on a mouthpiece of the apparatus.

47. The apparatus of claim 37, wherein the instructions, when executed, cause operations further comprising:
providing, to the user device, information regarding the apparatus, wherein the information comprises a type of vaporizable material contained in the apparatus, predefined user settings, and/or predefined operational settings.

48. A non-transitory computer readable medium comprising a memory storing instructions, wherein the instructions, when executed by at least one data processor, are configured to cause the at least one data processor to execute a method comprising:
  receiving, by a vaporizer device in communication with a user device, operational data indicative of a selected session size and a selected temperature for a vaporizer session, wherein the vaporizer device comprises a controller, wireless communication circuitry, heater control circuitry, and a heating element;
  causing the vaporizer device to operate consistent with the operational data indicative of the selected session size and the selected temperature; and
  providing, by the vaporizer device and to the user device, status data indicative of a status of the vaporizer session;
  wherein the selected session size selection and the selected temperature are locked when the vaporizer session is in progress such that the selected session size and the selected temperature are not adjustable while the vaporizer session is in progress.

49. A method, comprising:
  accessing, through operation of an application executing on one or more programmable processors, information regarding a vaporizer device;
  displaying, on a user interface generated on a display by the one or more programmable processors, one or more adjustable parameters for a vaporizer session of the vaporizer device, wherein the one or more adjustable parameters comprises a session size;
  receiving, by the one or more programmable processors, a selection of the one or more adjustable parameters;
  providing, by the one or more programmable processors and to a controller of the vaporizer device, data indicative of the selection, wherein the data indicative of the selection comprises operational settings to cause the vaporizer device to operate consistent with the selection; and
  locking, by the one or more programmable processors and in response to a determination that the vaporizer session is in progress, the session size such that the session size is not adjustable via the user interface while the vaporizer session is in progress.

50. The method of claim 49, wherein the one or more adjustable parameters comprises the session size, wherein the display of the session size comprises a dropdown menu comprising a plurality of selectable session size options for the vaporizer session, and wherein the selection of the session size comprises selecting, via user interaction, one of the plurality of selectable session size options.

51. The method of claim 49, wherein the one or more adjustable parameters comprises a temperature, wherein the display of the temperature comprises a slideable selection bar comprising a slideable icon, and wherein the selection of the temperature comprises positioning, via user interaction, the slideable icon at a temperature point along the slideable selection bar.

52. The method of claim 49, wherein the one or more adjustable parameters further comprises a temperature; and wherein the temperature is further locked in response to the determination that the vaporizer session is in progress such that the temperature is not adjustable via the user interface while the vaporizer session is in progress.

53. An apparatus, comprising:
  at least one data processor; and
  at least one memory storing instructions which, when executed by the at least one data processor, cause operations comprising:
    accessing, through operation of an application executing on the at least one data processor, information regarding a vaporizer device;
    displaying, on a user interface generated on a display by the at least one data processor, one or more adjustable parameters for a vaporizer session of the vaporizer device, wherein the one or more adjustable parameters comprises a session size;
    receiving, by the at least one data processor, a selection of the one or more adjustable parameters;
    providing, by the at least one data processor and to a controller of the vaporizer device, data indicative of the selection, wherein the data indicative of the selection comprises operational settings to cause the vaporizer device to operate consistent with the selection; and
    locking, by the at least one data processor and in response to a determination that the vaporizer session is in progress, the session size such that the session size is not adjustable via the user interface while the vaporizer session is in progress.

54. The apparatus of claim 53, wherein the one or more adjustable parameters comprises the session size, wherein the display of the session size comprises a dropdown menu comprising a plurality of selectable session size options for the vaporizer session and wherein the selection of the session size comprises selecting, via user interaction, one of the plurality of selectable session size options.

55. The apparatus of claim 53, wherein the one or more adjustable parameters comprises a temperature, wherein the display of the temperature comprises a slideable selection bar comprising a slideable icon, and wherein the selection of the temperature comprises positioning, via user interaction, the slideable icon at a temperature point along the slideable selection bar.

56. A non-transitory computer readable medium comprising a memory storing instructions, wherein the instructions, when executed by at least one data processor, are configured to cause the at least one data processor to execute a method comprising:
  accessing, through operation of an application executing on the at least one data processor, information regarding a vaporizer device;
  displaying, on a user interface generated on a display by the at least one data processor, one or more adjustable parameters for a vaporizer session of the vaporizer device, wherein the one or more adjustable parameters comprises a session size;
  receiving, by the at least one data processor, a selection of the one or more adjustable parameters;
  providing, by the at least one data processor and to a controller of the vaporizer device, data indicative of the selection, wherein the data indicative of the selection comprises operational settings to cause the vaporizer device to operate consistent with the selection; and
  locking, by the at least one data processor and in response to a determination that the vaporizer session is in progress, the session size such that the session size is not adjustable via the user interface while the vaporizer session is in progress.

* * * * *